(12) United States Patent
Fallin et al.

(10) Patent No.: US 7,594,923 B2
(45) Date of Patent: Sep. 29, 2009

(54) LINE LOCK SUTURE ATTACHMENT SYSTEMS AND METHODS

(75) Inventors: T. Wade Fallin, Hyde Park, UT (US);
M. Mary Sinnott, Logan, UT (US)

(73) Assignee: Medicine Lodge, Inc, Logan, UT (US)

( * ) Notice: Subject to any disclaimer, the term of this patent is extended or adjusted under 35 U.S.C. 154(b) by 1001 days.

(21) Appl. No.: 11/001,866

(22) Filed: Dec. 1, 2004

(65) Prior Publication Data
US 2005/0288711 A1     Dec. 29, 2005

Related U.S. Application Data

(63) Continuation-in-part of application No. 10/942,275, filed on Sep. 15, 2004, and a continuation-in-part of application No. 10/936,376, filed on Sep. 7, 2004, now Pat. No. 7,566,339, and a continuation-in-part of application No. 10/459,375, filed on Jun. 11, 2003, now Pat. No. 7,150,757.

(51) Int. Cl.
*A61B 17/04* (2006.01)
*A61B 17/58* (2006.01)
*A61B 17/82* (2006.01)
*F16G 11/00* (2006.01)

(52) U.S. Cl. .................. 606/232; 606/74; 606/103; 24/129 R

(58) Field of Classification Search ............ 606/74, 606/103, 148, 222, 232; 24/115 R, 129 R, 24/130, 129 B, 129 W; 289/13, 14, 17; 206/63.3
See application file for complete search history.

(56) References Cited

U.S. PATENT DOCUMENTS

| | | | |
|---|---|---|---|
| 757,820 A | * | 4/1904 | Lykke ................. 24/130 |
| 1,452,338 A | | 4/1923 | Flowers |
| 1,806,162 A | | 5/1931 | Hahn |
| 2,441,336 A | | 5/1948 | Sova |
| 3,409,014 A | | 11/1968 | Shannon |
| 3,678,543 A | | 7/1972 | Hobbs |
| 3,715,782 A | | 2/1973 | Newell |

(Continued)

FOREIGN PATENT DOCUMENTS

EP        861050 B1    6/2004

(Continued)

*Primary Examiner*—Julian W Woo
(74) *Attorney, Agent, or Firm*—David W. Meibes; Barbara Daniels; Daniel F. Justin

(57) ABSTRACT

A line lock includes a body at least partially bounding a plurality of passageways such that a suture can only be drawn through the passageways along one direction. The suture is attached to the line lock prior to use in surgery, either by securing one end of the suture to the line lock, or by retaining a loop of the suture with one of the passageways. A needle may be pre-attached to a free end of the suture. The suture may be inserted through the passageways through the use of a cartridge designed to contain the line lock. A threader may pass through the line lock within the cartridge along the desired pathway for the suture. Thus, the suture may be coupled to the threader and drawn through the passageways along the desired pathway by pulling the threader from the cartridge.

39 Claims, 21 Drawing Sheets

U.S. PATENT DOCUMENTS

| | | | |
|---|---|---|---|
| 3,785,009 A | 1/1974 | Nysten | |
| 3,857,645 A * | 12/1974 | Klein | 24/129 R |
| 3,880,166 A | 4/1975 | Fogarty | |
| 3,910,281 A | 10/1975 | Kletschka et al. | |
| 3,976,079 A | 8/1976 | Samuels et al. | |
| 4,034,443 A | 7/1977 | Turner | |
| 4,105,349 A | 8/1978 | Kupperman et al. | |
| 4,280,435 A | 7/1981 | Loomis | |
| 4,477,947 A | 10/1984 | Lyons | |
| 4,480,357 A | 11/1984 | Cummins | |
| 4,480,358 A | 11/1984 | Barling et al. | |
| 4,646,394 A | 3/1987 | Krauss | |
| 4,785,509 A | 11/1988 | Fisher | |
| 4,831,692 A | 5/1989 | Chuan | |
| 4,910,934 A | 3/1990 | Hennings | |
| 4,932,962 A | 6/1990 | Yoon et al. | |
| 4,976,013 A | 12/1990 | Wax | |
| 5,074,874 A | 12/1991 | Yoon et al. | |
| 5,123,913 A | 6/1992 | Wilk et al. | |
| 5,139,520 A | 8/1992 | Rosenberg | |
| 5,210,911 A | 5/1993 | Brown | |
| 5,284,485 A | 2/1994 | Kammerer et al. | |
| 5,306,301 A | 4/1994 | Graf et al. | |
| 5,374,269 A | 12/1994 | Rosenberg | |
| 5,403,330 A | 4/1995 | Tuason | |
| 5,445,167 A | 8/1995 | Yoon et al. | |
| 5,527,341 A | 6/1996 | Gogolewski et al. | |
| 5,572,770 A | 11/1996 | Boden | |
| 5,601,557 A | 2/1997 | Hayhurst | |
| 5,630,824 A | 5/1997 | Hart | |
| 5,645,588 A | 7/1997 | Graf et al. | |
| 5,653,719 A | 8/1997 | Raiken | |
| 5,693,060 A | 12/1997 | Martin | |
| 5,725,556 A | 3/1998 | Moser et al. | |
| 5,741,281 A | 4/1998 | Martin | |
| 5,741,301 A | 4/1998 | Pagedas | |
| 5,752,964 A | 5/1998 | Mericle | |
| 5,759,189 A | 6/1998 | Ferragamo et al. | |
| 5,769,894 A | 6/1998 | Ferragamo | |
| 5,782,864 A | 7/1998 | Lizardi | |
| 5,839,768 A | 11/1998 | Wackerly | |
| 5,891,168 A | 4/1999 | Thal | |
| 5,931,855 A | 8/1999 | Buncke | |
| 5,950,284 A | 9/1999 | Persson | |
| 6,024,758 A | 2/2000 | Thal | |
| 6,030,007 A | 2/2000 | Bassily et al. | |
| 6,045,574 A | 4/2000 | Thal | |
| 6,066,160 A | 5/2000 | Colvin et al. | |
| 6,095,282 A | 8/2000 | Sadeck | |
| 6,106,545 A | 8/2000 | Egan | |
| 6,132,439 A | 10/2000 | Kontos | |
| 6,171,317 B1 | 1/2001 | Jackson et al. | |
| 6,241,749 B1 * | 6/2001 | Rayhanabad | 606/232 |
| 6,319,271 B1 | 11/2001 | Schwartz et al. | |
| 6,432,123 B2 | 8/2002 | Schwartz et al. | |
| 6,485,065 B2 | 11/2002 | Lusk et al. | |
| 6,533,802 B2 | 3/2003 | Bojarski et al. | |
| 6,652,561 B1 | 11/2003 | Tran | |
| 6,739,450 B2 * | 5/2004 | Roshdy et al. | 206/63.3 |
| 6,749,616 B1 | 6/2004 | Nath | |
| 6,770,076 B2 | 8/2004 | Foerster | |
| 2002/0123758 A1 | 9/2002 | Bachman et al. | |
| 2004/0015171 A1 | 1/2004 | Bojarski et al. | |
| 2004/0098053 A1 | 5/2004 | Tran | |
| 2004/0133217 A1 | 7/2004 | Watschke | |
| 2004/0133238 A1 | 7/2004 | Cerier | |
| 2004/0133239 A1 | 7/2004 | Singhatat | |
| 2004/0138683 A1 | 7/2004 | Shelton et al. | |
| 2004/0138706 A1 | 7/2004 | Abrams et al. | |
| 2004/0153103 A1 | 8/2004 | Schwartz et al. | |
| 2007/0233241 A1 | 10/2007 | Graf et al. | |

FOREIGN PATENT DOCUMENTS

| | | |
|---|---|---|
| EP | 1430840 A2 | 6/2004 |
| GB | 2 046 826 A | 11/1980 |
| JP | 6-114067 | 4/1994 |
| WO | WO2004062506 A1 | 7/2004 |

* cited by examiner

LINE LOCK SUTURE ATTACHMENT SYSTEMS AND METHODS

CROSS-REFERENCE TO RELATED APPLICATIONS

This application is a continuation-in-part of U.S. patent application Ser. No. 10/459,375, filed on Jun. 11, 2003 now U.S. Pat. No. 7,150,757 and entitled ADJUSTABLE LINE LOCKS AND METHODS. This application is also a continuation-in-part of U.S. patent application Ser. No. 10/936,376, filed on Sep. 7, 2004 now U.S. Pat. No. 7,566,339 and entitled ADJUSTABLE LINE LOCKS AND METHODS. This application is also a continuation-in-part of U.S. patent application Ser. No. 10/942,275, which is identified by filed on Sep. 15, 2004 and entitled LINE LOCK THREADING SYSTEMS AND METHODS. The disclosures of all of the above are incorporated herein by reference.

BACKGROUND OF THE INVENTION

1. The Field of the Invention

The present invention relates generally to devices to replace knots and more specifically to devices to replace surgical knots tied in open, arthroscopic, and endoscopic procedures.

2. The Relevant Technology

Numerous devices have been developed to eliminate the need to tie knots as a way of securing a line. The devices that accomplish the same function as a knot, which is in part to secure a line to retain tension in a portion of the line, are typically referred to as line locks.

Line locks generally operate in one of two ways. Some line locks are manually actuated to secure one or more lines so that tension is maintained in a portion of the line(s). Once actuated, the line lock resists sliding along the line(s) either toward or away from the tensioned portion of the line. Other line locks are continuously adjustable in one direction so that tension is increased in the portion of the line upon which the line lock is advanced. The continuously adjustable line locks resist movement away from the tensioned portion of the line, but can be further advanced toward the tensioned portion of the line with an appropriately applied force.

The portion of a line that is put under tension, typically to secure some object, is commonly referred to as the standing end. The portion of the line that extends toward the line handler is commonly referred to as the working end. A knot in a line, or a line lock attached to a line, is the demarcation between the standing end and the working end.

Continuously adjustable line locks offer several advantages. They are passive locking devices, meaning that no other operation is required to secure the line lock once it is moved along the line to its desired position. Furthermore, these line locks can be used to continuously increase the tension in the standing end until it reaches a desired level of tension.

The advantages of line locks over tied knots are very attractive in many varied applications, including the use of surgical sutures. However, the line locks developed to date have many deficiencies when considered for surgical suture applications. For example, many known line locks for surgical applications are somewhat small, and as a result, they have small passageways that are positioned quite close to each other. This makes it somewhat difficult to thread the suture through the line lock in the proper pattern. Furthermore, the user must select and apply the correct suture because improper suture selection can impair the locking and/or strength of the attachment system. Additionally, the proper needle must be attached to the suture. Thus, there are multiple selection and assembly steps that must be performed prior to use of the attachment system.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to line locks that can be used in part to replace surgical knots tied in sutures in open, arthroscopic, and endoscopic procedures. By increasing the size of the line locks, it is also appreciated that the line locks can be used outside of surgical procedures for any use where it is desired to selectively adjust and/or tie off a line such as a rope, cord, string, or other conventional type of line.

Figure 1:
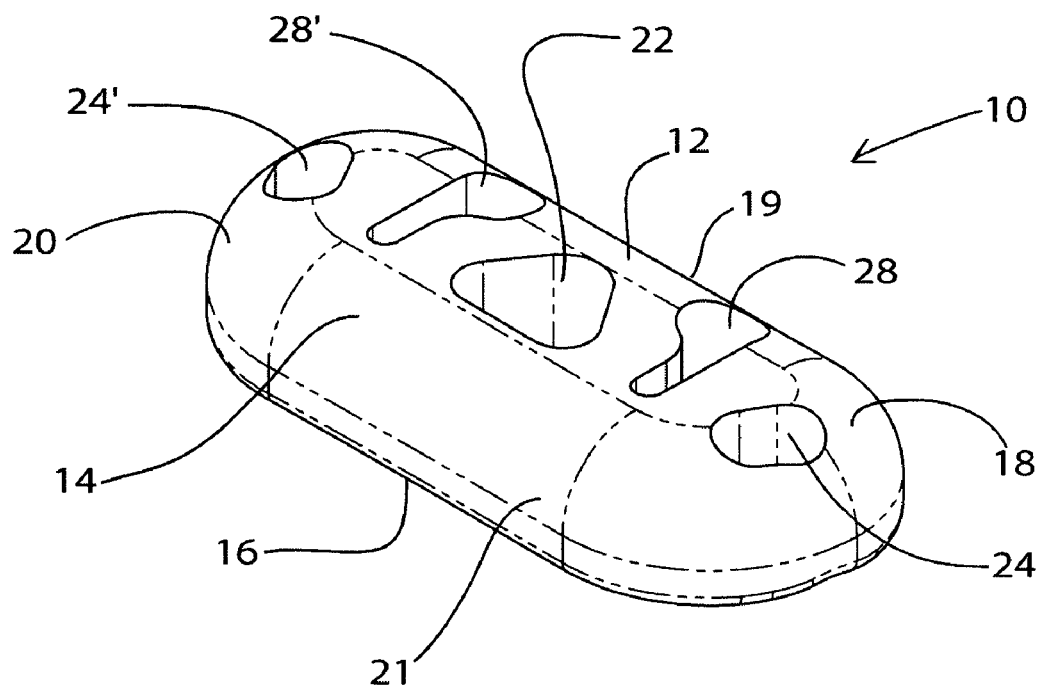
FIG. 1 is a perspective view of an adjustable line lock.

Depicted in FIG. 1 is one embodiment of a line lock 10 incorporating features of the present invention. Line lock 10 comprises an elongated body 12 having a top surface 14 and an opposing bottom surface 16 that each extend between a first end 18 and an opposing second end 20. Body 12 also has a first side 19 and an opposing second side 21 extending between first end 18 and second end 20. In the embodiment depicted, body 12 has a substantially rectangular configuration with rounded ends. As will be apparent from the following disclosure, however, body 12 can be any desired configuration such as triangular, circular, square or any other polygonal or irregular configuration.

In typical surgical applications, body 12 has a maximum dimension D along its length (FIG. 2) which is typically less than about 2 cm, more commonly less than about 1.5 cm, and even more commonly less than about 1 cm. Other dimensions can also be used. By way of example and not by limitation, in one embodiment body 12 has a height in a range between about 1 mm to about 1.5 mm, a width in a range between about 2 mm to about 3 mm, and length D in a range between about 5 mm to about 8 mm. In non-surgical applications, body 12 can be any desired dimension. For example, maximum dimension D can be in a range from about 5 cm to about 0.5 m. Again, other dimensions can also be used.

For use in surgical applications, body 12 can be comprised of any biocompatible material. The biocompatible material can be bioabsorbable or non-bioabsorbable. Examples of typical materials include non-bioabsorbable plastic, bioabsorbable plastic, synthetic tissue, and allograft tissue. In non-surgical applications, body 12 can be made of any desired material such as metal, plastic, wood, fiberglass, composite, or the like.

As depicted in FIG. 1, centrally extending through body 10 between top surface 14 and bottom surface 16 is a primary passageway 22. As used in the specification and appended claims, the term "passageway" is broadly intended to include closed apertures, such as depicted by primary passageway 22, partially bound apertures, open channels, recesses, grooves, slots, and the like, that are capable of receiving a line and at least partially retaining the line therein. Thus, in this application, a flat wall may not be termed a "passageway." The term "line" as used in the specification and appended claims is broadly intended to include suture, cord, rope, filament, wire, cable, and any other form of line.

Extending between surfaces 14 and 16 at first end 18 of body 12 is a first secondary passageway 24. A second secondary passageway 24' extends between surfaces 14 and 16 at second end 20. Extending through body 12 at a location between primary passageway 22 and first secondary passageway 24 is a first working passageway 28. In one embodiment, although not necessarily required, first working passageway 28 is disposed between primary passageway 22 and first secondary passageway 24 such that a geometric line segment 36 (FIG. 2) can be extended between primary passageway 22 and first secondary passageway 24 so that line segment 36 intersects with first working passageway 28. Similar to first working passageway 28, a second working passageway 28' extends through body 12 at a location between primary passageway 22 and second secondary passageway 24'.

Each working passageway 28 and 28' has an elongated transverse cross sectional area that extends between a first end 38 and an opposing second end 40. Each working passageway 28, 28' comprises an enlarged access region 32 at first end 38 which communicates with a constricted capture slot 34 at second end 40. Access region 32 is sized to enable easy feeding of a line into and through the corresponding working passageways 28, 28'. Accordingly, although access region 32 can be slightly smaller than the transverse cross sectional area of the line which is to be passed therethrough, access region 32 typically has a transverse cross sectional area that is equal to or slightly larger than the transverse cross sectional area of the line that is to be passed therethrough.

In contrast, capture slot 34 has a width W that is substantially equal to or less than the diameter of the line that is to be passed through working passageways 28, 28'. For example, in one embodiment width W is less than about 0.9 times the diameter of the line and more commonly less than about 0.75 times the diameter of the line. It is appreciated that working passageways 28, 28' can come in a variety of different configurations. For example, capture slot 34 can come in a variety of different constricted, tapered, or notched shaped configurations that are capable of securely retaining a line through wedged engagement. For line made of less compressible material, such as metal, the required difference between the width W and the diameter of the line may be less than the examples given above.

Figure 2:
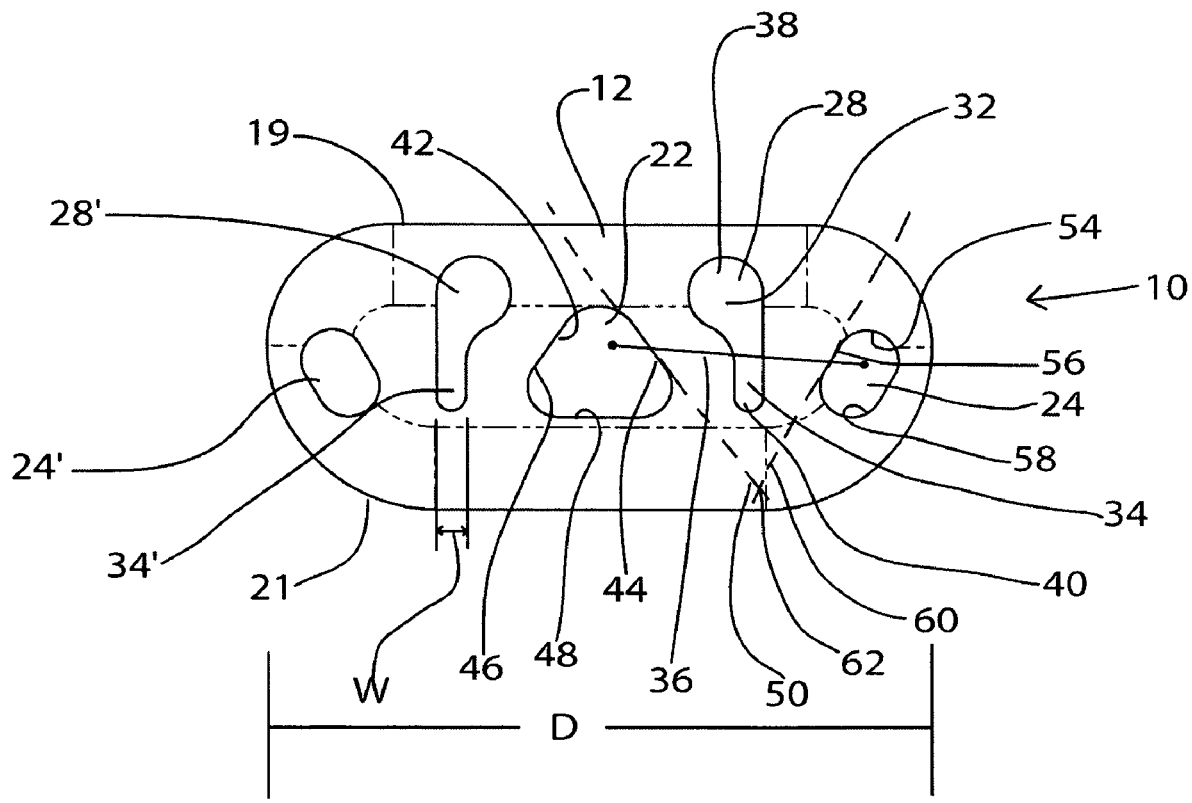
FIG. 2 is a top plan view of line lock shown in FIG. 1.

As depicted in FIG. 2, central passageway 22 is bounded by an interior surface 42 of body 12 having a substantially triangular transverse cross section. Interior surface 42 comprises a first side face 44 disposed toward first working passageway 28, a second side face 46 disposed toward second working passageway 28' and which intersects with first side face 44, and a third side face 48 extending between first side face 44 and second side face 46. Although side faces 44 and 46 are shown as being substantially flat, in alternative embodiments side faces 44 and 46 can be curved or irregular. In one embodiment, however, first side face 44 is substantially disposed in or tangent to a first plane illustrated by dashed line 50. With reference to FIG. 2, plane 50 slopes toward second end 40 of first working passageway 28 as plane 50 extends from first side 19 of body 12 to second side 21.

First secondary passageway 24 is bounded by an interior surface 54 of body 12 having an elongated transverse cross section. Interior surface 54 comprises a first side face 56 disposed toward first working passageway 28 and an opposing second side face 58. Although side faces 56 and 58 are shown as being substantially flat, in alternative embodiments side faces 56 and 58 can also be curved or irregular. Again, in one embodiment first side face 56 is substantially disposed in or tangent to a second plane illustrated by dashed line 60. With reference to FIG. 2, second plane 60 slopes toward second end 40 of first working passageway 28 as second plane 60 extends from first side 19 of body 12 to second side 21.

In the above discussed configuration, first plane 50 and second plane 60 are disposed so as to be converging as they extend from first side 19 of body 12 to second side 21. In the embodiment depicted, planes 50 and 60 intersect at a location 62 on body 12 that is at least substantially aligned with a central longitudinal axis of capture slot 34. In other embodiments, location 62 can be directly adjacent to body 12 or at a distance from body 12. Likewise, location 62 need not be aligned with the central longitudinal axis of capture slot 34. Although not required, in one embodiment planes 50 and 60 are disposed at equally opposing angles relative to the central longitudinal axis of capture slot 34. Furthermore, planes 50 and 60 can intersect so as to form an inside angle therebetween in a range between about 5° to about 85°.

Second secondary passageway 24' has substantially the same configuration as first secondary passageway 24. Likewise, second secondary passageway 24' has substantially the same relative position to second working passageway 28' and second side face 46 of primary passageway 22 as first secondary passageway 26 has to first working passageway 28 and first side face 44 of primary passageway 22. As such, the discussion with regard to planes 50 and 60 are also applicable to primary passageway 22 and second secondary passageway 24'.

By way of example of the passageways and not by limitation, for use with a size USP #2 braided suture, which has a diameter in a range between about 0.5 mm to about 0.6 mm, primary passageway 22 has a length in a range between about 1.3 mm to about 1.5 mm and a width in a range between about 1 mm to about 1.3 mm. Secondary passageways 24 and 24' have a width of about 0.8 mm and a length in a range between 1 mm to about 1.3 mm. Access region 32 of working passageways 28 and 28' have width in a range between about 0.7 mm to 1 mm while capture slots 17 have a width in a range between about 0.3 mm to 0.4 mm.

Figure 3:
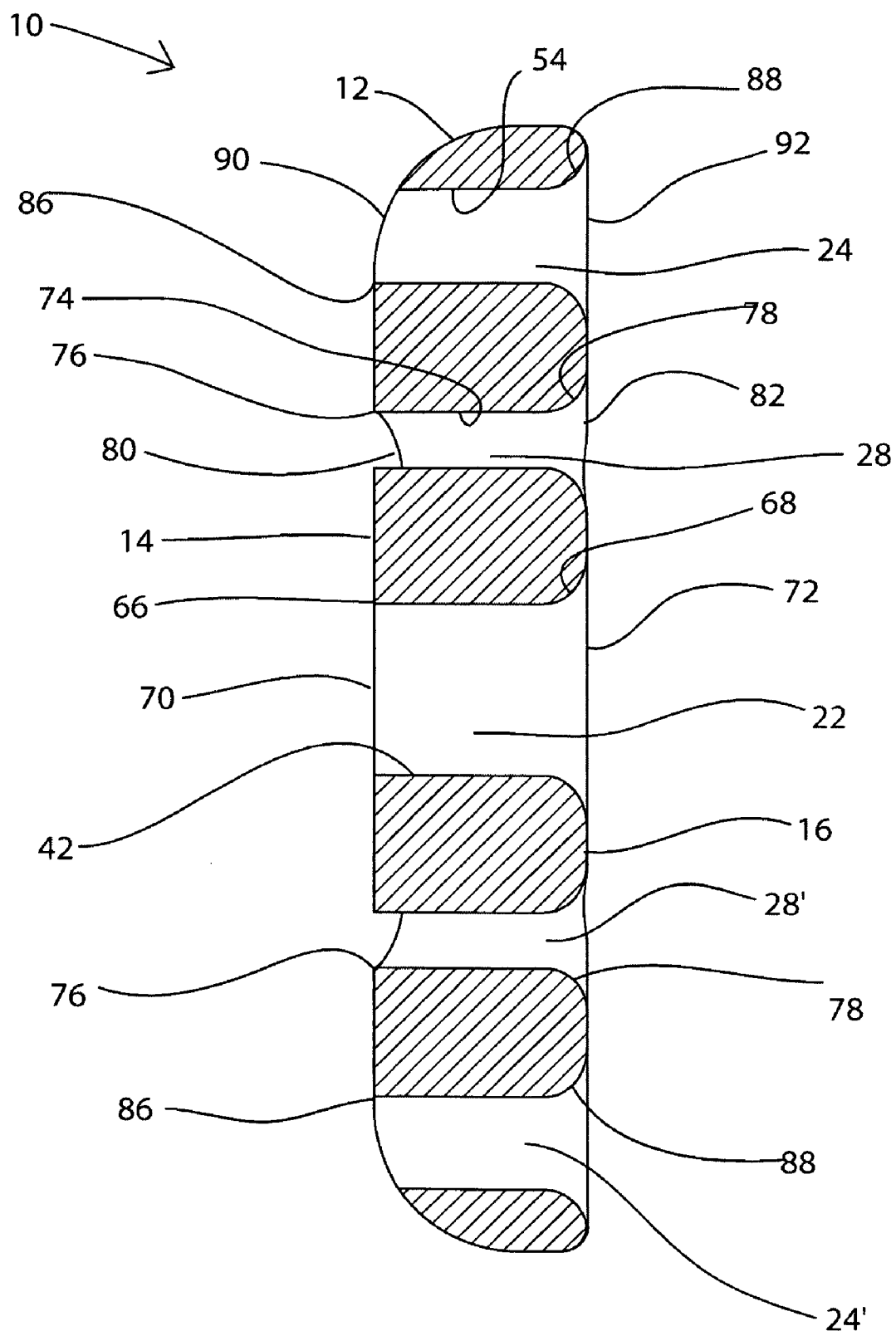
FIG. 3 is an elevated cross sectional side view of the line lock shown in FIG. 1.

Depicted in FIG. 3, interior surface 42 of primary passageway 22 extends to a top outside corner 66 and an opposing bottom outside corner 68. Top outside corner 66 bounds a top primary opening 70 while bottom outside corner 66 bounds a bottom primary opening 72. Similarly, first working passageway 28 has an interior surface 74 that extends to a top outside corner 76 and an opposing bottom outside corner 78. Top outside corner 76 bounds a top working opening 80 while bottom outside corner 76 bounds a bottom working opening 82. Likewise, interior surface 54 of first secondary passageway 24 extends to a top outside corner 86 and an opposing bottom outside corner 88. Top outside corner 86 bounds a top secondary QS t opening 90 while bottom outside corner 86 bounds a bottom secondary opening 92.

For reasons as will be discussed below in greater detail, each of top outside corners 66, 76, and 86 has a radius of curvature that is smaller than the radius of curvature of the corresponding bottom outside corners 68, 78, 88. By way of example and not by limitation, in one embodiment top outside corners 66, 76, and 86 each have a radius of curvature in a range between about 0 mm to about 1 mm with about 0 mm to about 0.5 mm being more common. In contrast, bottom outside corners 68, 78, and 88 each have a radius of curvature in a range between about 0.25 mm to about 2 mm with about 0.5 mm to about 1.5 mm being more common. Other dimensions can also be used, particularly outside of the surgical area. In yet other embodiments it is appreciated that the top outside corners and the bottom outside corners can have the same radius of curvature or that only one or more of the top outside corners may be smaller than one or more of the bottom outside corners. In still other embodiments, it is appreciated that only a portion of one or more of the top outside corners may be smaller than a portion of one or more of the bottom outside corners.

It is again noted that second secondary passageway 24' and second working passageway 28' having substantially the same configuration as first secondary passageway 24 and first working passageway 28, respectively. As such, the same discussion with regard to the outside corners are also applicable thereto. Likewise, like elements are identified by like reference characters.

Figure 4A:
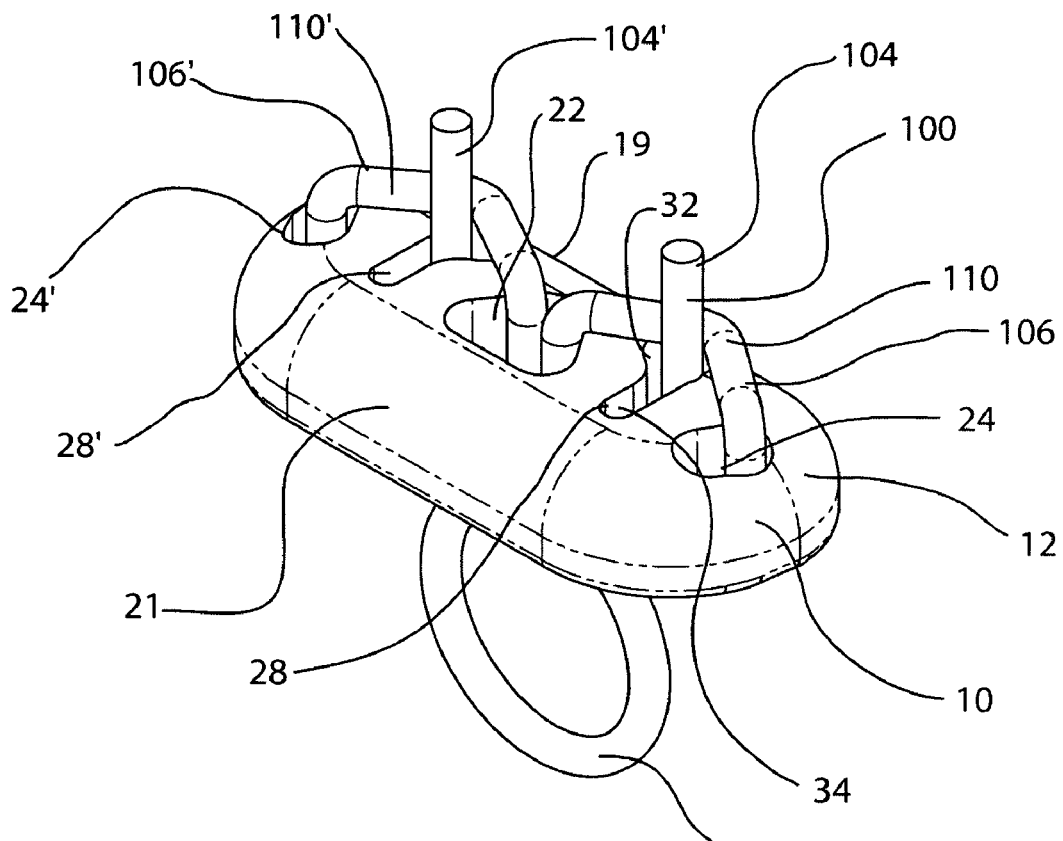
FIG. 4A is a perspective view of the line lock shown in FIG. 1 with a line routed therethrough in a slack unlocked position.

Depicted in FIG. 4A is a line 100 adjustably mounted on line lock 12. Line 100 comprises a standing portion 102 in the form of a loop which extends below primary passageway 22, a first working portion 104 which extends out of first working passageway 28, and a first locking portion 106 extending therebetween. It is appreciated that each of the sections 102, 104, and 106 of line 100 are relative to each other in that they change as line 100 is adjusted on line lock 10. Line 100 further includes a second working portion 104' which extends out of second working passageway 28' and a second locking portion 106' that extends between standing portion 102 and second working portion 104'.

First locking portion 106 extends up through primary passageway 22, down through first secondary passageway 24, and then up through first working passageway 28. The section of locking portion 106 extending between primary passageway 22 and first secondary passageway 24 is referred to as compression section 110. Line 100 passes up through first working passageway 28 so that first working portion 104 is disposed between compression section 110 and capture slot 34. Second locking portion 106' is similarly passed through passageways 22, 24', and 28'.

During use, standing portion 102 of line 100 is typically looped around, embedded within, or passed through tissue, or some other structure. To secure standing portion 102 to the structure, unwanted slack is removed from standing portion 102. This is accomplished by sliding line lock 10 over standing portion 102 and/or pulling on working portion 104 and/or 104' so that the unwanted slack is pulled through line lock 10. In either event, at least one of working portions 104 and 104' increases in length while standing portion 102 shortens.

In the configuration depicted in FIG. 4A, line 100 is passing through enlarged access regions 32 of working passageways 28 and 28'. In this position, relative locking portions 106 and 106' freely slide through corresponding passageways of line lock 10 as the unwanted slack from standing portion 102 is removed. A mild tension force is typically applied to working portions 104 and 104' as the unwanted slack is removed. The applied force pushes compression section 110 and 110' back toward first side 19 of body 12 and thus away from capture slots 34, 34'. In turn, the portion of line 100 passing through primary passageway 22 and secondary passageways 24 and 24' also naturally slides back within the passageways toward first side 19 of body 12. This movement of line 100 helps to decrease frictional resistance on line 100.

Figure 4B:
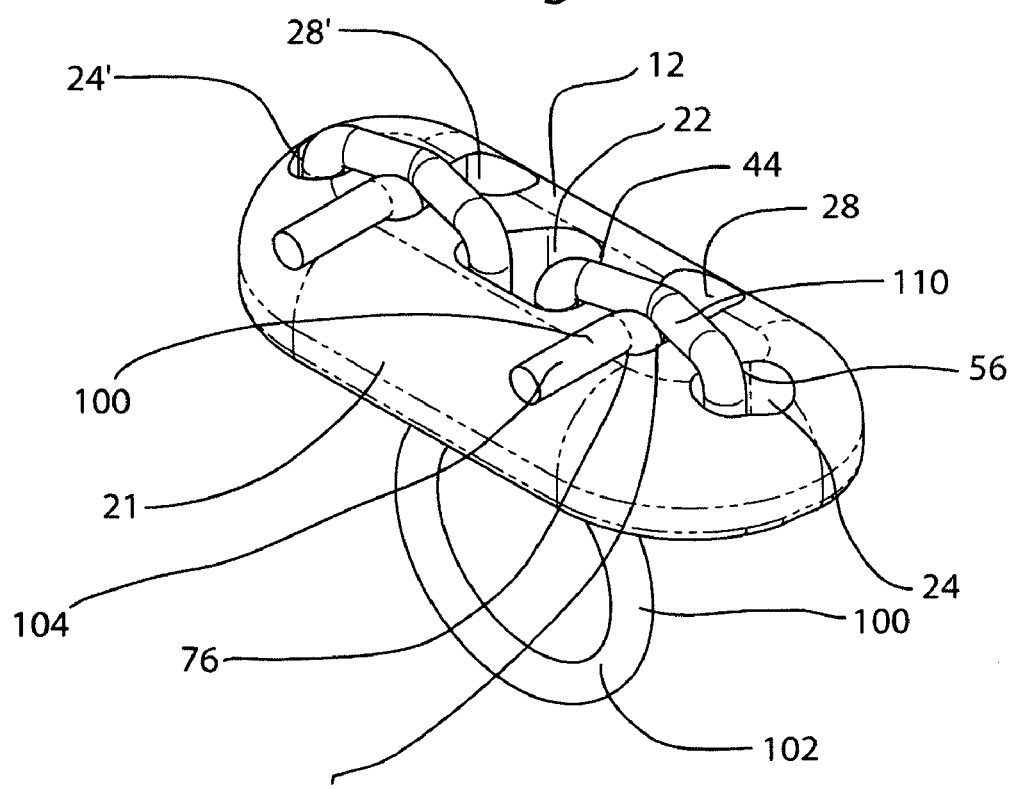
FIG. 4B is a perspective view of the line lock shown in FIG. 4A with the line in a tensioned locked position.

Once the slack is removed from standing portion 102, further force is applied to working portions 104, 104' and/or line lock 10 so as to tension locking portions 106, 106' on line lock 10. As depicted in FIG. 4B, as line 100 is tensioned, the diverging side face 44 of primary passageway 22 and side face 56 of first secondary passageway 24 cause the portions of line 100 passing therethrough, and thus compression portion 110 extending therebetween, to slide toward first side 21 of body 12.

Furthermore, as line 100 is tensioned, compression portions 1110, 110' are shortened causing them to move into a more linear orientation. As a result of the above, tensioning of line 100 causes compression portions 110, 110' to force working portions 104, 104' toward corresponding capture slots 34, 34'. In turn, at least a portion of line 100 within working passageways 28 and 28' is forced into corresponding capture slots 34, 34' so that line 100 is secured therein by wedged frictional engagement. That is, line 100 is secured by compression within capture slots 34, 34' because line 100 has a diameter larger than the width of capture slots 34, 34'. Once line 100 is captured under compression in capture slots 34, 34', line 100 will remain captured even if there is a complete loss of tension in standing end 102. Thus, "locking" of line lock 10 to line 100 ensures that line lock 10 will not become separated from line 100, even under cyclic changes in line tension in standing end 102. Furthermore, line lock 10 is continuously adjustable in that further tension can be applied to standing portions 104 and/or 104' at any time to remove additional slack from standing portion 102 while retaining line 100 locked to line lock 10.

The passageways extending through line lock 10 are also configured such that as compression portions 110 and 110' force line 100 into capture slots 34 and 34', compression portions 110 and 110' also fold and/or bias working ends 104 and 104' over and/or against top outside corner 76 of capture slots 34 and 34'. In view of the relatively small radius of curvature of top outside corner 76, the engagement between the captured working ends 104 and 104' and top outside corner 76 creates a high degree of friction which forms a secondary locking mechanism between line 100 and line lock 10. As such, the engagement between capture working ends 104 and 104' and top outside corner 76 prevents backward movement of line lock 10 relative to line 100.

In the embodiment depicted in FIG. 4B, compression portion 110 is disposed above a portion of top outside corner 76 so as to directly bias working ends 104 against top outside corner 76. Compression portion 110 is also shown disposed directly above a portion of working end 104 that is biasing against top outside corner 76. In alternative embodiments, compression portion 110 when tensioned can extend between central passageway 22 and secondary passageways 24 without passing over working passageway 28. That is, compression portion 110 can pass at a location toward second side 21 of line lock 10 that is spaced apart from working passageway 28. In this embodiment, compression portion 110 still passes over working end 104, thereby remotely causing working end 104 to fold over and bias against top outside corner 76.

One of the unique features of the present embodiment is that as line lock 10 is advanced toward standing end 102 when standing end 102 is not under tension, i.e., when slack is being removed from standing end 102, working ends 104 and 104' tend to push away compression portions 110 and 110', as discussed above, thereby minimizing frictional engagement between working ends 104, 104', compression portions 110, 110' and line lock 10. As a result, line lock 10 can be easily advanced on line 100.

Furthermore, unlike some other continuously adjustable line locks known in the art that use a loop portion to draw in and wedge a portion of a line within a bore hole, compression portions 110 and 110' traverse a substantially straight path because they are constrained by secondary passageways 24 and 24' and primary passageway 22. This substantially straight path translates to a lower frictional resistance to sliding not possible with other adjustable line locks known in the art.

As previously discussed, line 100 is routed through passageways 22, 24, and 28 so as to pass over the outside corners of the passageways. When a tensioned section of line 100 passes around a first outside corner of line lock 10, friction produced between line 100 and the corresponding outside corner cause a decrease in tension on the portion of line 100 extending away from the outside corner on the side opposite the tensioned section. The friction produced at the outside corner must be overcome in order to cause line 100 to slide. Similarly, as the line passes around subsequent outside corners away from the tensioned section, each subsequent corner produces an incremental decrease in line tension and a corresponding incremental increase in friction that must be overcome to cause line 100 to slide. The loss in tension and increase in friction diminishes for each subsequent corner. Thus, the first corners are the most significant.

Figure 6:
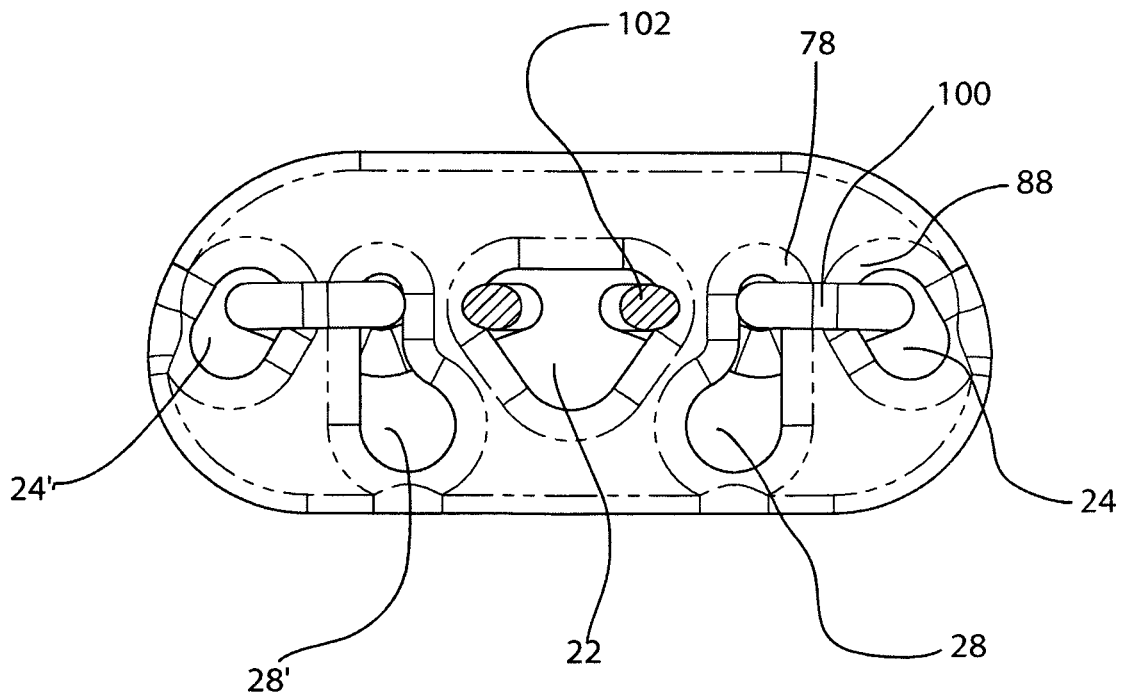
FIG. 6 is a bottom plan view of the line lock shown in FIG. 4B.

As depicted in FIG. 6, in view of the above discussion, when working end 104 is tensioned and standing end 102 is slack, line 100 extending from working end 104 toward line lock 10 first turns on bottom outside corner 78 of working passageway 28 and bottom outside corner 88 of secondary passageway 24. As a result of the fact that these are the closest outside corners to tensioned working end 104, outside corners 78 and 88 will produce the highest frictional resistance. Accordingly, to minimize the frictional resistance produced by outside corners 78 and 88 and thereby ease the sliding of line lock 10 toward standing end 102, outside corners 78 and 88 are generously rounded as previously discussed.

Figure 5:
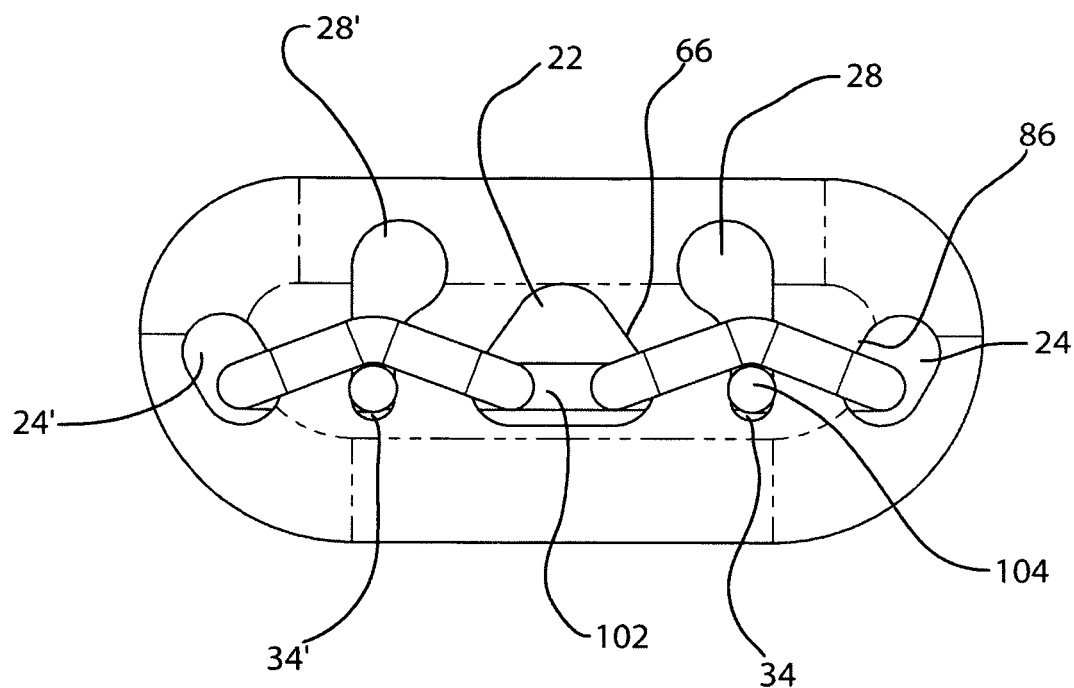
FIG. 5 is a top plan view of the line lock shown in FIG. 4B.

In contrast, as depicted in FIG. 5, when standing end 102 is tensioned and working end 104 is slack, line 100 extending from standing end 102 toward line lock 10 first turns on top outside corner 66 of primary passageway 22 and top outside corner 86 of secondary passageway 24. In view of the fact that these are the closest outside corners to tensioned standing end 102, outside corners 66 and 86 will produce the highest frictional resistance. Accordingly, to maximize the frictional resistance produced by outside corners 66 and 86 and thereby minimizing slipping of line 100 once tensioned, outside corners 66 and 86 are formed relative sharp as previously discussed. More specifically, top outside corners 66 and 86 have a smaller radius of curvature than bottom outside corners 78 and 88. It is noted that not all of each outside corner that bounds a corresponding opening has to have the same radius of curvature. For example, the portion of each outside corner that directly engages line 100 can have a radius of curvature that is different from the remainder of the corresponding outside corner.

Figure 7:
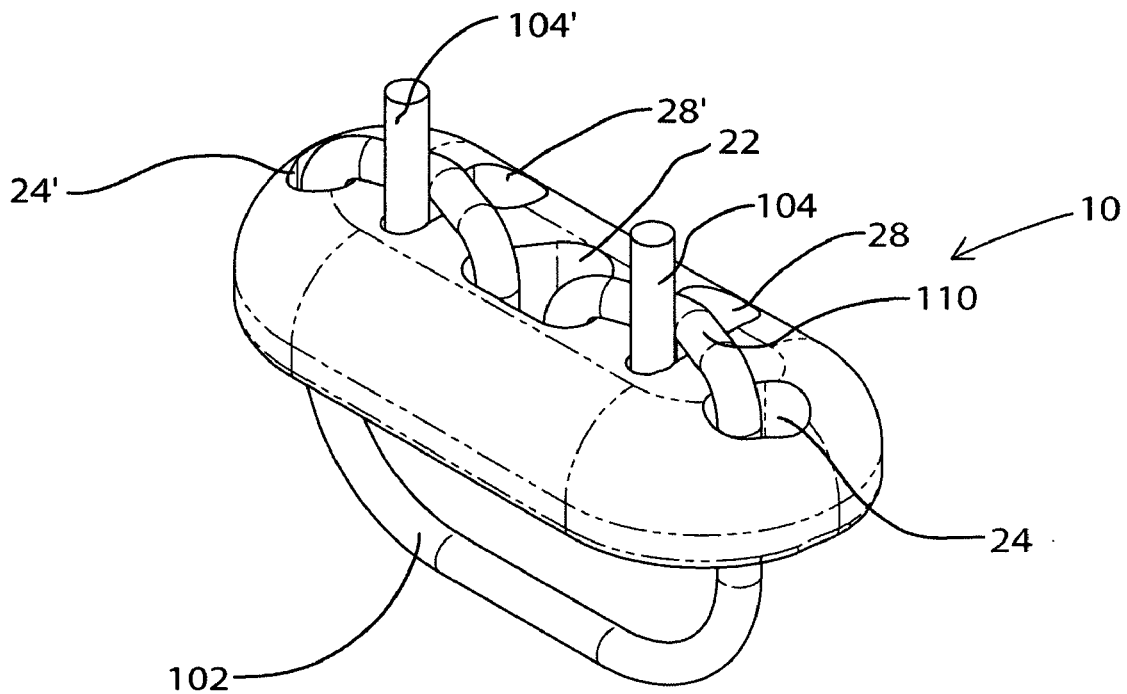
FIG. 7 is a perspective view of the line lock shown in FIG. 4A with the line routed in a different path.

Depicted in FIG. 7, line lock 10 is shown having an alternative routing of line 100. To achieve this routing, working ends 104 and 104' are passed up through secondary passageways 24 and 24', respectively, down through primary passageway 22, and then back up through working passageways 28 and 28', respectively. Again compression portions 110 and 110' are formed that selectively force working ends 104 and 104' toward capture slots 34 as discussed above. In yet another alternative, it is appreciated that one end of line 100 can be routed as shown in FIG. 4A while the opposing end of line 100 is routed as shown in FIG. 7.

Figure 8:
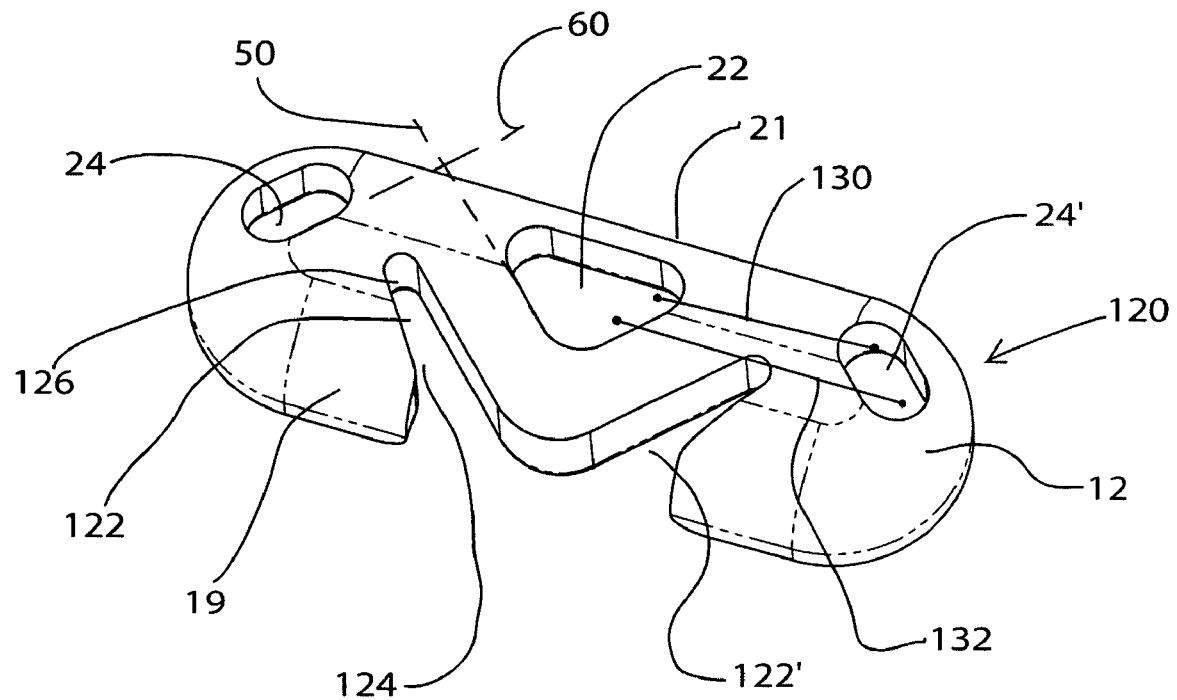
FIG. 8 is a perspective view of an alternative embodiment of the line lock shown in FIG. 1 with open working passageways.

Depicted in FIG. 8 is an alternative embodiment of a line lock 120. It is noted that all common elements of alternative embodiments of line locks disclosed herein are identified by like reference characters. Line lock 120 comprises body 12 having primary passageway 22 and secondary passageways 24 and 24' extending therethrough as discussed above with regard to FIG. 1. In contrast to the circumferentially closed working passageways 28, 28', however, line lock 120 comprises working passageways 122 and 122' that are circumferentially open. That is, each working passageway 122 and 122' comprises an elongated tapered slot having a first end 124 and an opposing second end 126. First end 124 is open along first side 19 of body 12 to facilitate convenient loading of line 100 therein. First end 124 also typically has a width greater than the diameter of line 100. Second end 126 extends to a location between primary passageway 22 and a corresponding one of secondary passageway 24, 24'.

In this embodiment it is noted that the passageways are positioned such that a geometric line segment 130 can be extended between primary passageway 22 and secondary passageway 24' such that line segment 130 does not intersect with working passageway 122'. However, a geometric line segment 132 can also be extended between primary passageway 22 and secondary passageway 24' such that line segment 132 intersects with working passageway 122'. Second end 126 of each working passageway 122, 122' typically has a width substantially equal to or smaller than the diameter of line 100.

Figure 9:
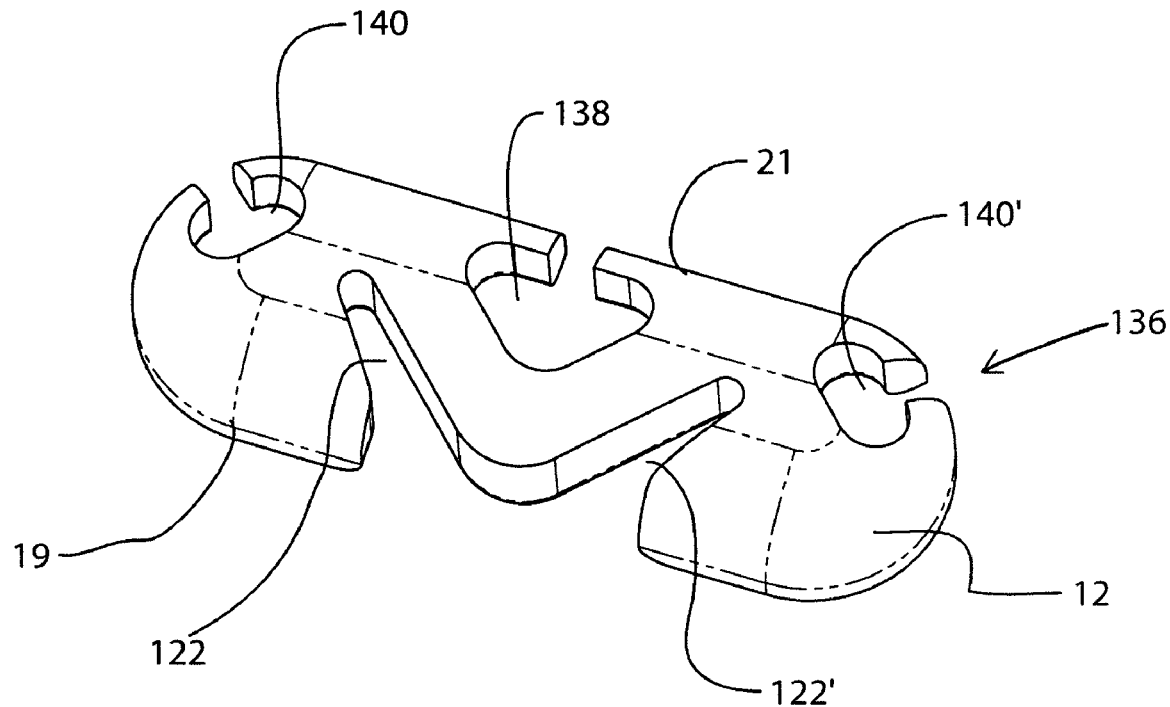
FIG. 9 is a perspective view of another alternative embodiment of the line lock shown in FIG. 1 with open passageways.

Depicted in FIG. 9 is another alternative embodiment of a line lock 136 having substantially the same configuration as line lock 120. In contrast to the circumferentially bounded primary passageway 22 and secondary passageways 24 and 24' of line lock 120 in FIG. 8, however, line lock 136 comprises a partially bounded primary passageway 138 which is open at second side 21 of body 12 and partially bounded secondary passageways 140 and 140' that are also each open at or adjacent to second side 21 of body 12.

Figure 10:
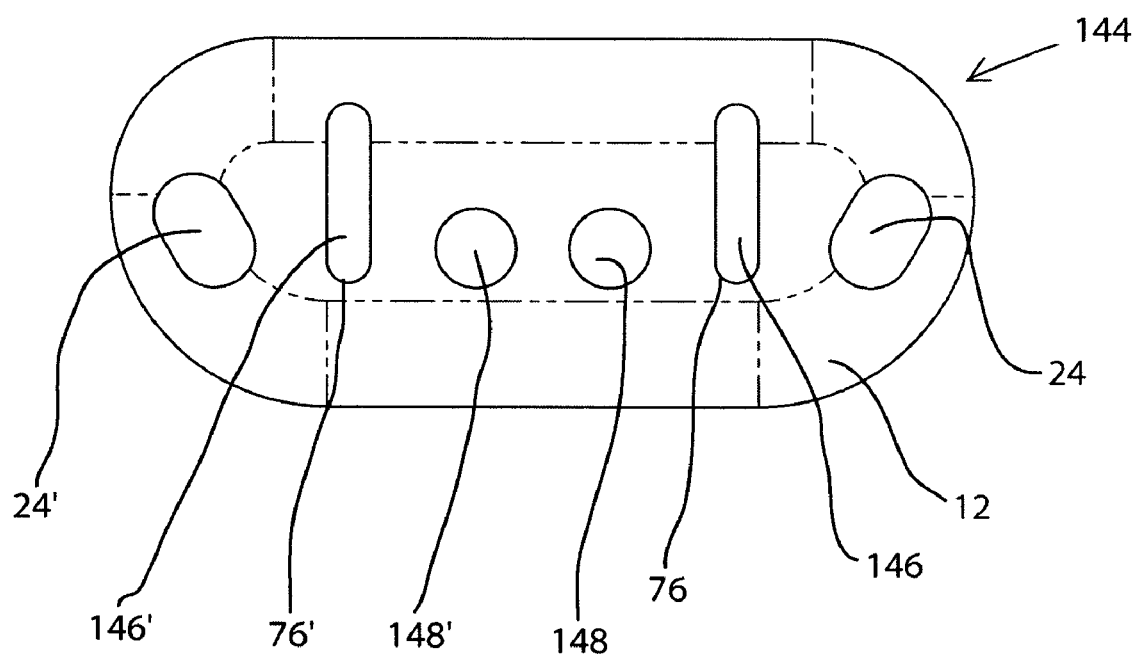
FIG. 10 is a perspective view of another alternative embodiment of the line lock shown in FIG. 1 with dual primary passageways and uniform working passageways.

Two separate locking features were previously discussed with regard to securing line 100 to line lock 10. Specifically, line 100 is secured by being wedged into capture slots 34 and 34' and by biasing working portions 104 and 104' against the top outside corner 76 of each working passageway 28, 28'. In alternative embodiments, it is appreciated that the locking features can be used independently. For example, depicted in FIG. 10 is a line lock 144 having body 12 with secondary passageways 24 and 24'. In contrast to line lock 10, however, line lock 144 comprises working passageways 146 and 146' wherein capture slots 34 have been eliminated. Working passageways 146 and 146' merely comprise elongated channels having a width substantially the same size or larger than the diameter of the line 100 to be passed therethrough. Line 100 is thus primarily secured to line lock 144 as a result of compression portions 110, 110' biasing line 100 against top outside corner 76 of each working passageways 146 and 146' as previously discussed.

Line lock 144 is also distinguished over line lock 10 in that primary passageway 22 has been replaced with a first primary passageway 148 and a spaced apart second primary passageway 148'. Primary passageways 148 and 148' operate with opposing ends of line 100. It is also noted that in alternative embodiments primary passageway(s) and/or the secondary passageways need not be elongated to allow the line passing therethrough to slide toward opposing sides 19 and 21 of body 12 as previously discussed with regard to line lock 10.

Figure 11:
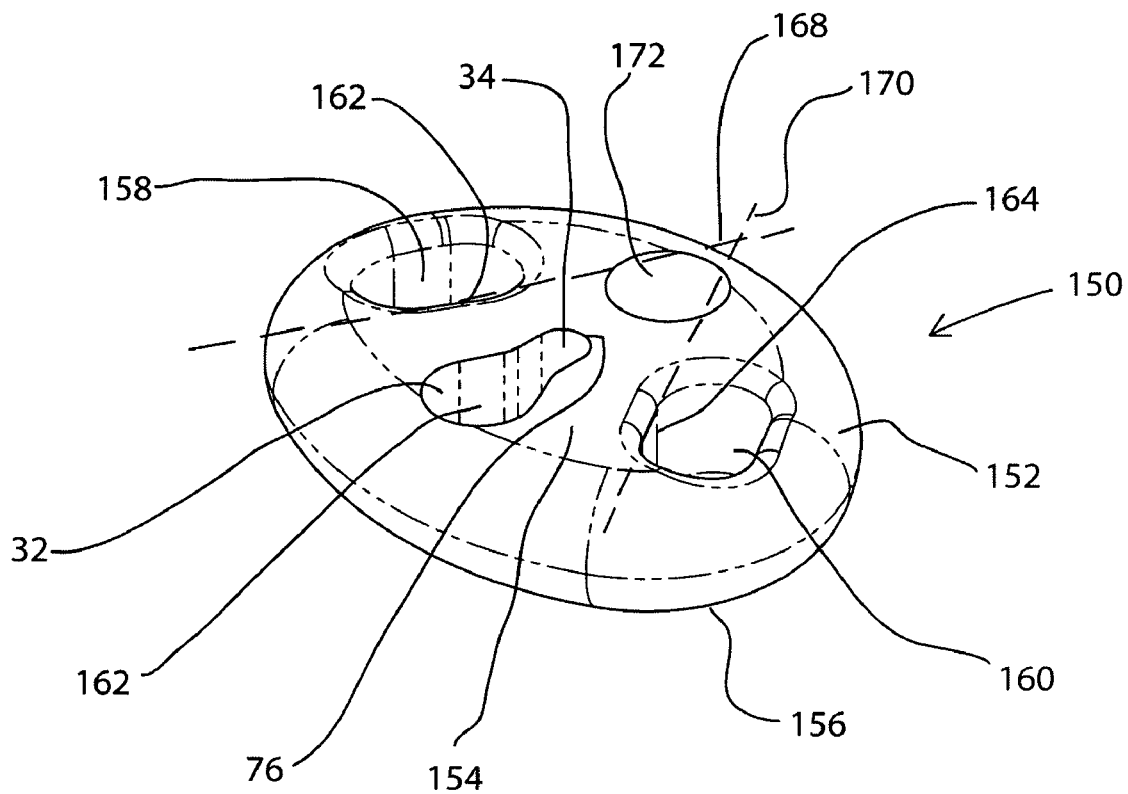
FIG. 11 is a perspective view of a line lock for use with a single strand of line.

Depicted in FIG. 11 is an alternative embodiment of a line lock 150 that is designed to slide along a single strand of line 100. Line lock 150 comprises a substantially disk shaped body 152 having a top surface 154 and an opposing bottom surface 156. Extending through body 152 between surfaces 154 and 156 is a primary passageway 158 and a spaced apart secondary passageway 160. Disposed between passageways 158 and 160 is a working passageway 162. Similar to line lock 10, working passageway 162 of line lock 150 has a first end with enlarged access region 32 and an opposing second end with constricted capture slot 34 thereat.

Primary passageway 158 and secondary passageway 160 have substantially the same elongated circular configuration which is similar to previously discussed secondary passageway 24. Each of passageways 158 and 160 has an inside face 162 and 164, respectively, that is disposed toward working passageway 162. Each inside face 162 and 164 is substantially disposed in or is tangent to a corresponding plane 168 and 170, respectively. Planes 168 and 170 converge toward capture slot 34 of working passageway 162 and diverge away from access region 32.

Also extending through body 152 between top surface 154 and bottom surface 156 is an end passageway 172. Although end passageway 172 can be positioned at a variety of different locations, end passageway 172 is shown aligned with working passageway 162 such that a plane extending between working passageway 162 and end passageway 172 separates primary passageway 158 from secondary passageway 160.

Figure 12A:
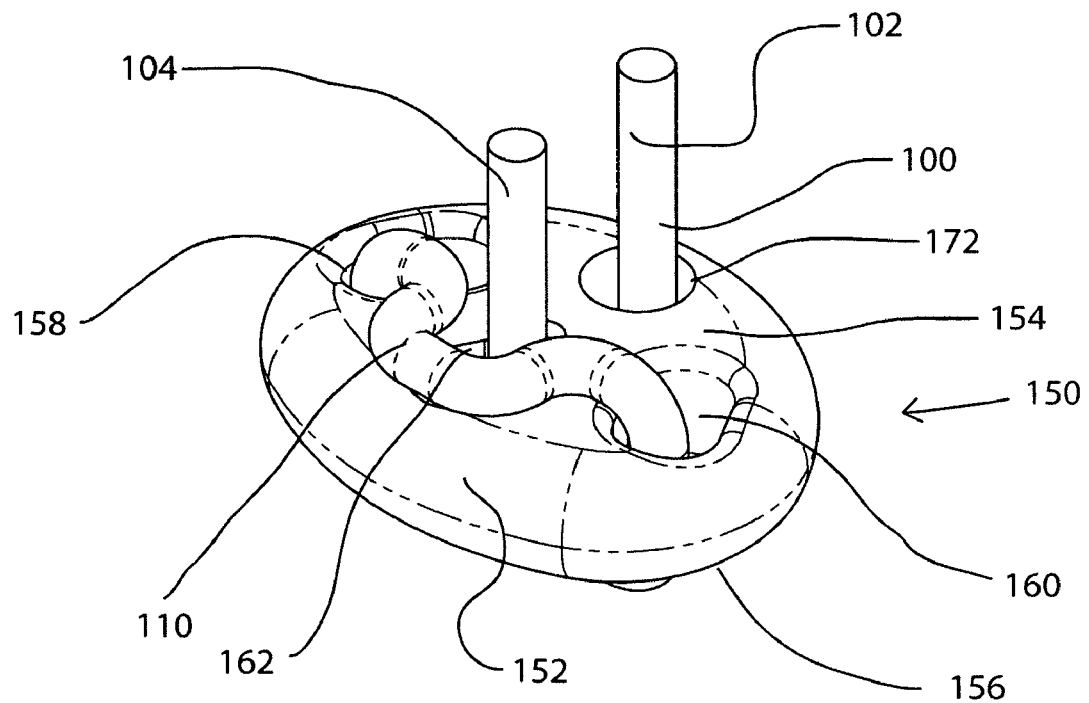
FIG. 12A is a perspective view of the line lock shown in FIG. 11 with a line routed therethrough.
Figure 12B:
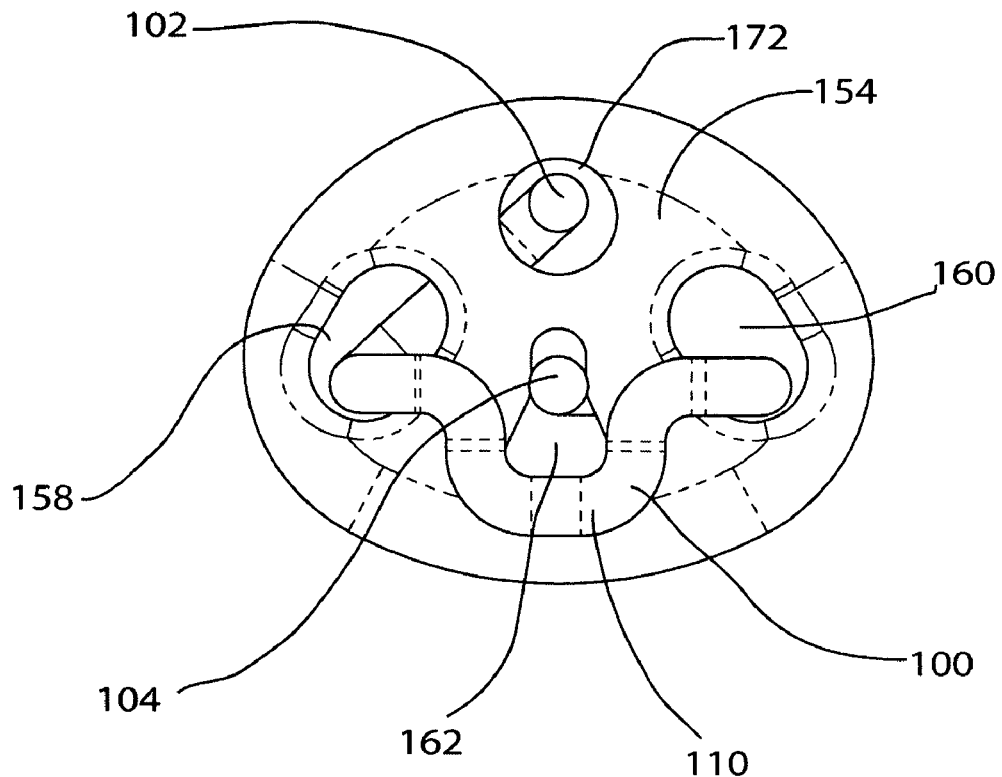
FIG. 12B is a top plan view of the line lock shown in FIG. 12A.
Figure 12C:
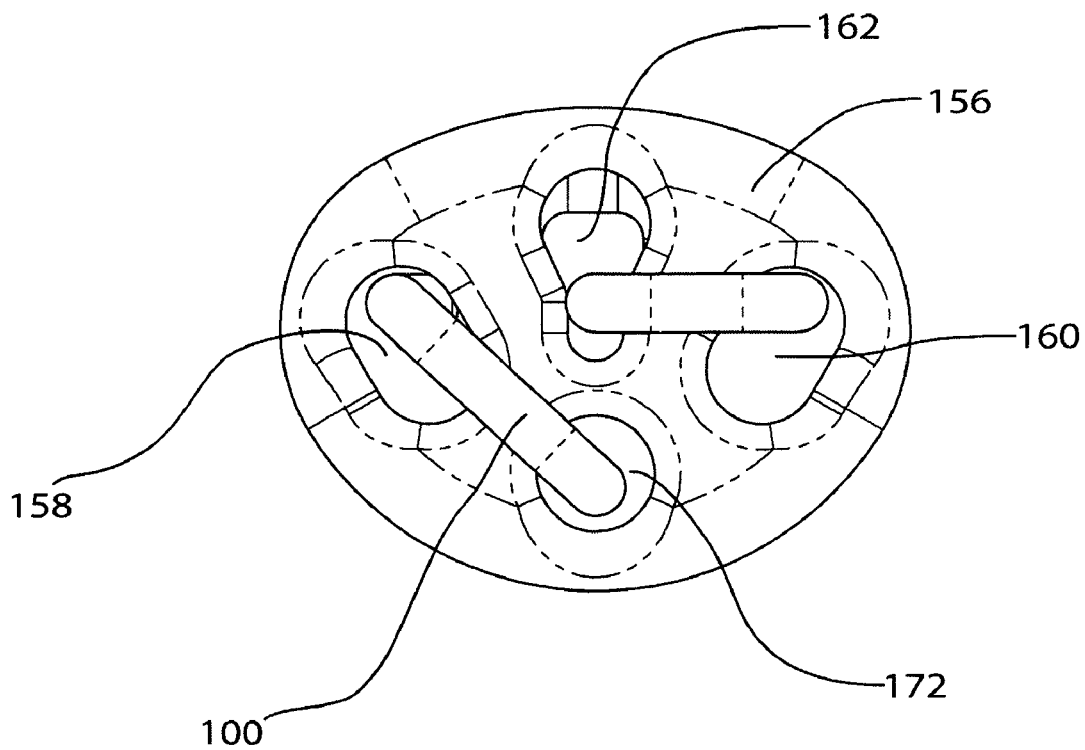
FIG. 12C is a bottom plan view of the line lock shown in FIG. 12A.

During use, as depicted in FIGS. 12A-12C, line 100 is routed through line lock 150 by passing working portion 104 from top surface 154 to bottom surface 156 through end passageway 172, up through primary passageway 158, down through secondary passageway 160, and finally up through working passageway 162. Compression portion 110 of line 100 extends between primary passageway 158 and secondary passageway 160 and is positioned to act upon working portion 104. Line lock 150 can be selectively advanced by pulling working portion 104 away from top surface 154 so that line 100 travels through line lock 150. Alternatively, line lock 150 can be manually slid toward standing portion 102. In either event, the length of standing portion 102 is decreased.

As line 100 is tensioned on line lock 150, line 100 locks on line lock 150 in substantially the same manner that line 100 locks with working passageway 28 as previously discussed with regard to line lock 10. That is, compression portion 110 forces working end 104 toward capture slot 34 so that the portion of line 100 within working passageway 162 is captured by wedged frictional engagement within capture slot 34. Furthermore, compression portion 110 either directly or indirectly biases working portion 104 against the top outside corner 76 of working passageway 162 at the second end thereof so as to increase the frictional engagement between line 100 and line lock 150. Line lock 150 thus provides a continuously adjustable line lock or a one way sliding stop. In alternative embodiments, it is appreciated that line lock 150 can be modified in at least the same ways as discussed with the other line locks disclosed herein.

The embodiment shown in FIGS. 12A-12C is advantageous in certain applications where line lock 150 is positioned behind a first object and working portion 104 and standing portion 102 pass through the first object. In this situation, standing portion 102 is fixed to a second object. By pulling on working portion 104, the first object is drawn irreversibly toward the second object. This is an advantage with surgical sutures where standing end 102 of a suture is attached to normal tissues and line lock 150 is placed behind tissue that has torn away. Standing portion 102 and working portion 104 pass through the torn tissue toward the normal tissue. By pulling on working portion 104 of suture, the torn tissue is pulled into apposition with the normal tissues and line lock 150 maintains the torn tissue adjacent to the normal tissue to facilitate healing of the tissue.

Figure 13A:
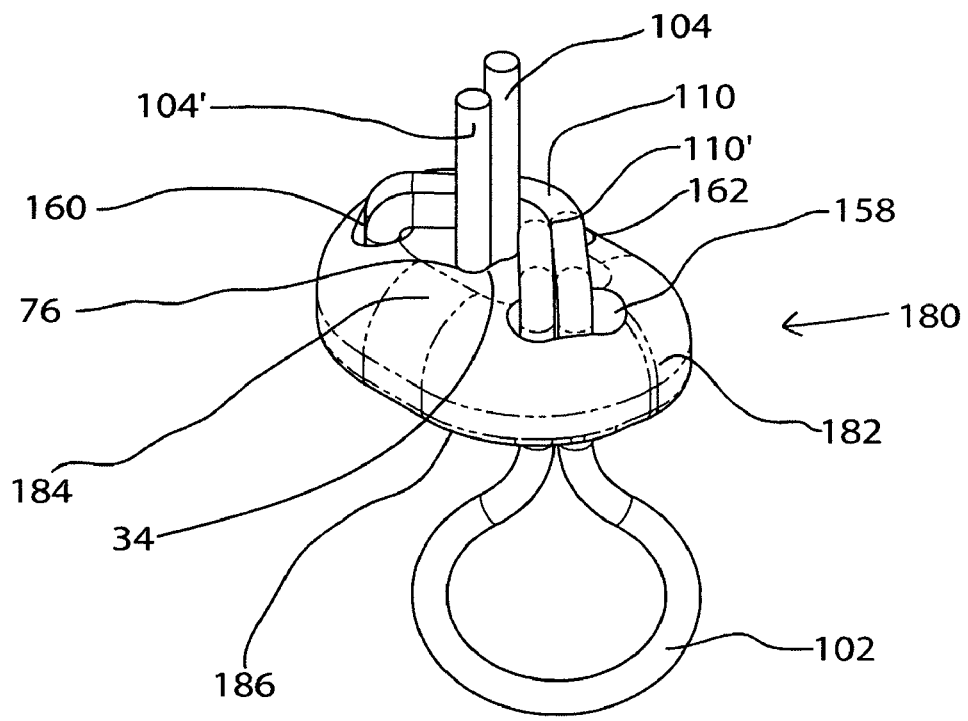
FIG. 13A is a top perspective view of a line lock having dual strands of line routed therethrough.
Figure 13B:
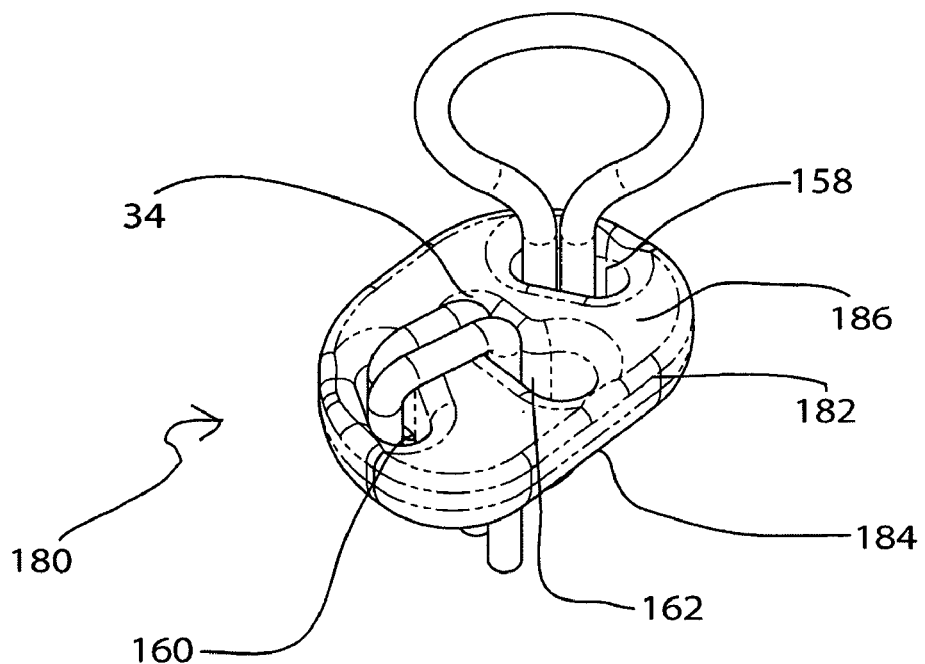
FIG. 13B is a bottom perspective view of the line lock shown in FIG. 13A.

Depicted in FIGS. 13A and 13B is another embodiment of a line lock 180 incorporating features of the present invention. Line lock 180 also comprises a substantially disk shaped body 182 having a top surface 184 and an opposing bottom surface 186. As with line lock 150, line lock 180 includes primary passageway 158, secondary passageway 160, and working passageway 162. Again, although not required, working passageway 162 is disposed such that a geometric line segment can be extended between primary passageway 158 and secondary passageway 160 so that the line segment intersects with working passageway 162. In contrast to line lock 150, line lock 180 does not include end passageway 172.

Each of passageways 158, 160, and 162 is configured to receive a double strand of line 100. Specifically, during use both working end 104 and 104' are passed up through primary passageway 158, down through secondary passageway 160 and then back up through working passageway 162. As a result, standing portion 102 is again formed in a loop that can be looped around, passed through, or otherwise secured to tissue or other structure. Unwanted slack is removed from standing portion 102 by again sliding line lock 180 on line 100 toward standing portion 102 and/or by pulling on one or both of working portions 104 and 104' so that line 100 passes through line lock 180.

When line 100 is tensioned on line lock 180, compression portions 110 and 110' force working portions 104, 104' toward capture slot 34 so that a portion of each line section passing through working passageway 162 is captured by wedged frictional engagement within capture slot 34. Compression portions 110 and 110' also bias working portions 104 and 104' toward and/or against top outsider corner 76 of working passageway 162 so as to increase the frictional engagement between line 100 and line lock 180. As previously discussed with passageways 22, 24, and 28 of line lock 10 in FIGS. 1-6, the radius of curvature of the top outside corner and bottom outside corner of each passageway 158, 160, and 162 can be set so as to further control the ability of line 100 to slide or not slide through the passageway. Other alternatives as discussed with the line locks herein are also applicable to line lock 180. In particular each of the passageways 158, 160, and 162 can also be configured to receive a single strand of line 100. In this configuration the single strand of line 100 is routed in a manner as described above for the double strand of line 100. Instead of the standing portion 102 forming a loop when a double strand of line 100 is used, in this case the standing portion 102 consists of a free end which can be attached to tissue or other structures.

Figure 14A:
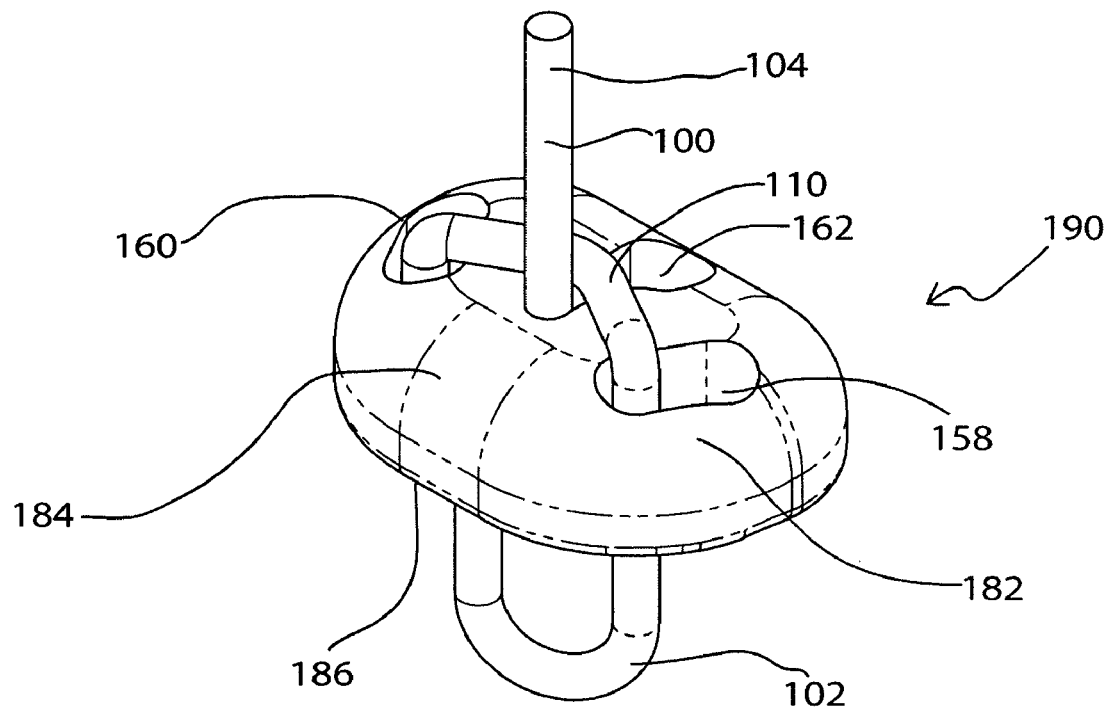
FIG. 14A is a top perspective view of a line lock having a line secured thereto.
Figure 14B:
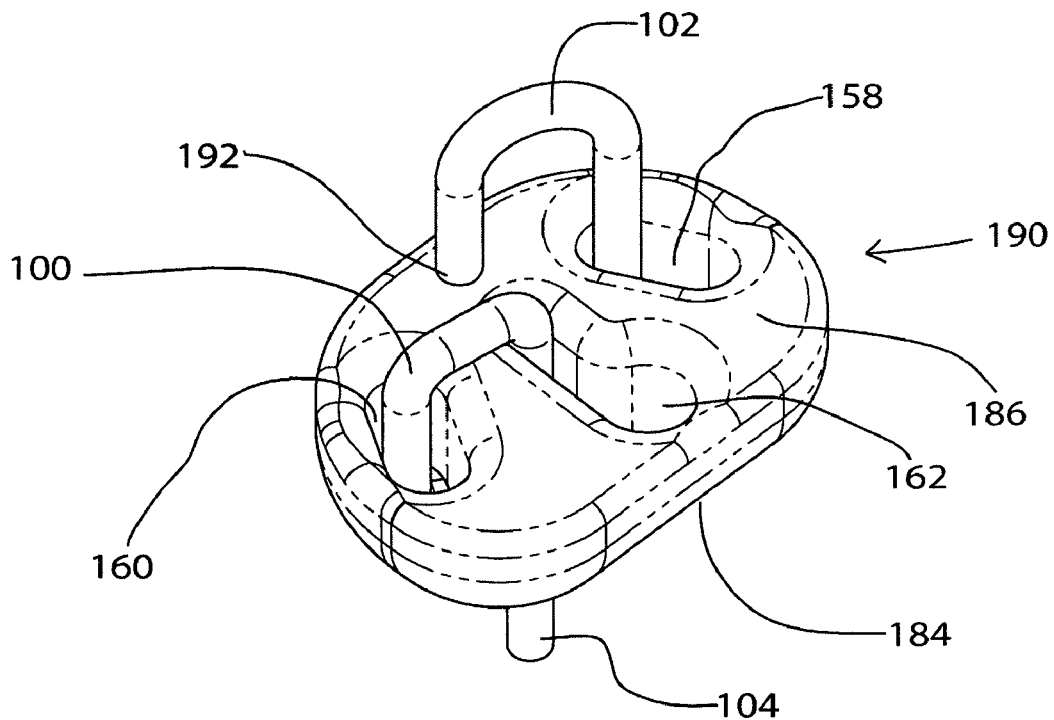
FIG. 14B is a bottom perspective view of the line lock shown in FIG. 14A.

Depicted in FIGS. 14A and 14B is still another embodiment of a line lock 190 incorporating features of the present invention. Line lock 190 has substantially the same configuration as line lock 180 with like elements being referenced with like reference characters. The primary distinction between line locks 180 and 190 is that in line lock 190, an end 192 of line 100 adjacent to standing portion 102 is secured to bottom surface 186 of body 182. End 192 can be secured to body 182 by being integrally molded into body 182 or can be otherwise secured such as by welding or mechanical attachment.

Line lock 190 is also distinguished from line lock 180 in that passageways 158, 160, and 162 need only be configured to receive a single strand of line 100. That is, working end 104 passes up through primary passageway 158, down through secondary passageway 160, and then back up through working passageway 162. Standing portion 102 is again substantially formed into a loop extending from end 192 of line 100 to primary passageway 158. Because end 192 of line 100 is secured to body 182, unwanted slack can be removed from standing portion 102 by pulling line 100 through line lock 190 and/or sliding line lock 190 down line 100.

Line 100 is locked to line lock 190 in substantially the same manner as discussed above with regard to the other line locks when line 100 is tensioned on line lock 190. More precisely, after the working portion 102 has been inserted through or wrapped around the tissue to be retained, the line lock 190 may be advanced while holding the working portion 104 of the line 100 to tighten the standing portion 102. Alternatively, the line lock 190 may be held in place while pulling on the working portion 104. An insertion device (not shown) may be used to hold or advance the line lock 190.

As tension in the standing portion 102 increases, the compression section 110 tightens and presses the underlying working portion 104 against the body 182. The pressure on the working portion 104 keeps the working portion 104 from moving back into the working passageway 162, thereby keeping the standing portion 102 from loosening. Thus, the tissue will be securely retained by the standing portion 102, even after the working portion 104 has been cut short.

Pre-attachment of one end of a suture to a line lock, i.e., attachment of the suture prior to the surgical use, has a number of benefits. More specifically, it expedites installation of the suture and the line lock because separate sutures and line locks need not be located and assembled. As will be illustrated subsequently, a needle may also be pre-attached to the working end 104 of the line 100 so that all items needed for the suturing portion of the operation are ready for use. The line lock 190 may even be contained in a threader cartridge designed to facilitate insertion of the line 100 through the passageways 158, 160, 162 along the pattern illustrated. The configuration and use of such an assembly will be shown subsequently, in connection with FIG. 21.

In the embodiment of FIGS. 14A and 14B, the end 192 may advantageously be attached to the line lock 190 via insert molding. According to one manufacturing method, the end 192 is positioned within an injection mold (not shown) used to form the line lock 190. As the selected polymer fills the mold, it surrounds the end 192. Then, as the selected polymer cools and hardens, it captures the end 192 in a substantially permanent manner.

The present invention contemplates the use of any known attachment method, including but not limited to insert molding, adhesive bonding, knotting, ultrasonic welding, looping, swaging, and fastening via mechanical fasteners such as bolts and clips, and the like. FIGS. 15 through 20 provide examples of embodiments in which such alternative attachment methods are used.

Figure 15:
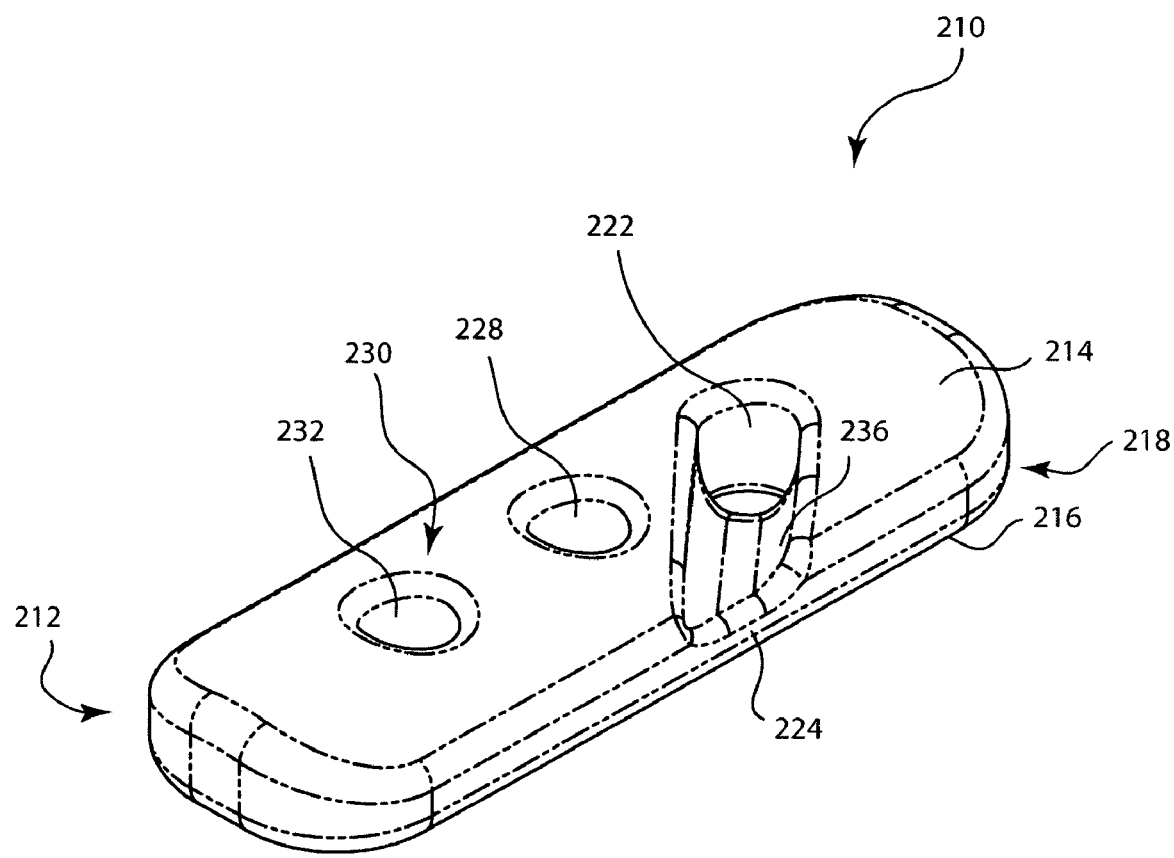
FIG. 15 is a perspective view of a line lock according to another embodiment of the invention.

Referring to FIG. 15, a perspective view illustrates a line lock 210 according to one alternative embodiment of the invention. The line lock 210 has a body 212 with a generally rectangular shape, with a top surface 214, a bottom surface 216, and a periphery 218 that separates the top surface 214 from the bottom surface 216. The body 212 fully bounds a primary passageway 222 and partially bounds a secondary passageway 224. In the embodiment of FIG. 15, the secondary passageway 224 is defined by a portion of the periphery 218 of the body 212.

The body 212 also fully bounds a working passageway 228 and a retention passageway 230. The retention passageway 230 has a bore 232 positioned to retain one end of a suture (not shown in FIG. 15). The body 212 further defines a groove 236 extending between the primary and secondary passageways 222, 224. The operation of the various passageways 222, 224, 228, 230 and the groove 236 will be described in connection with FIGS. 16 and 17.

Figure 16:
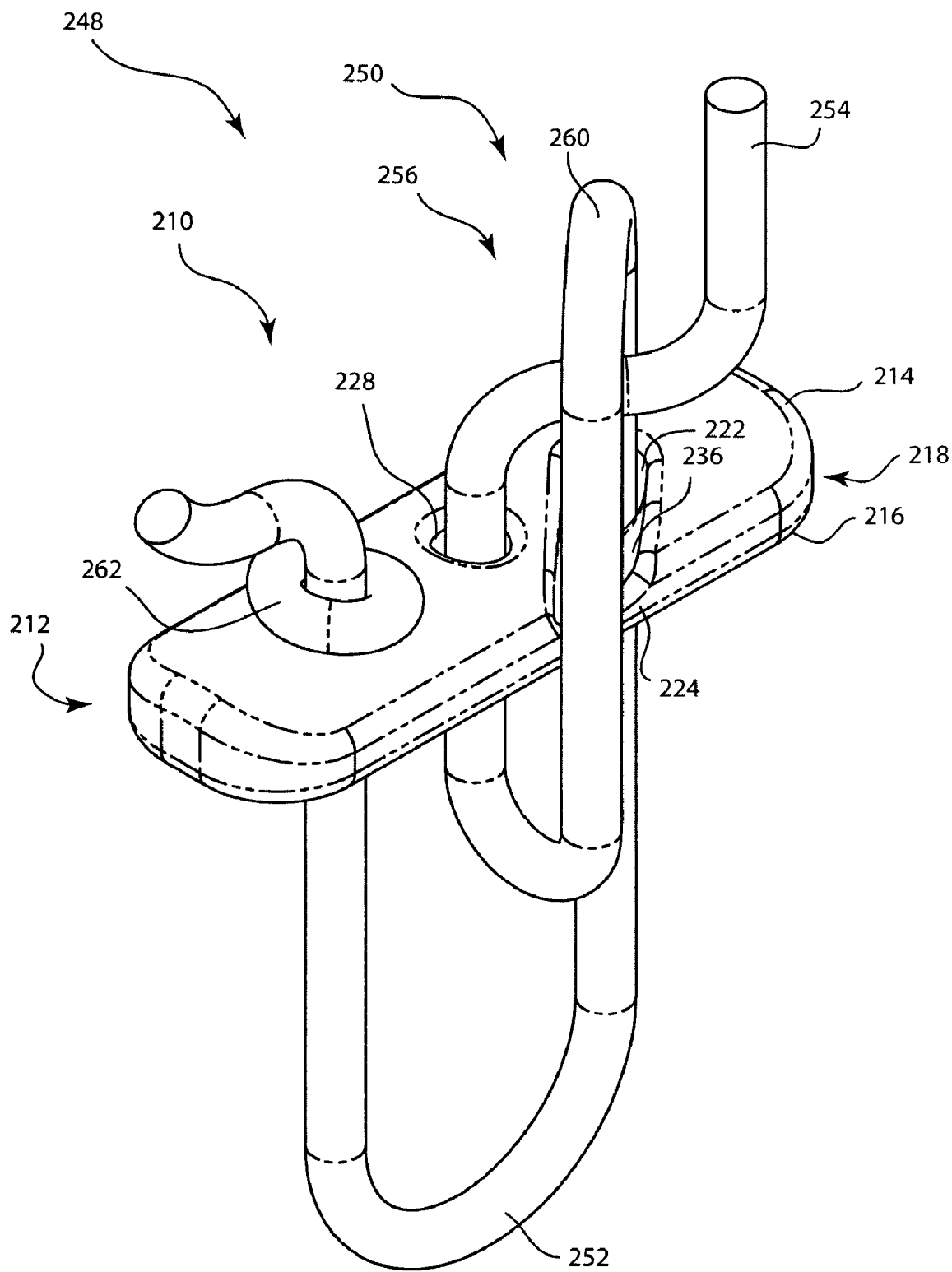
FIG. 16 is a perspective view of the line lock of FIG. 15, with a suture threaded loosely therethrough.

Referring to FIG. 16, a perspective view illustrates a system 248 including the line lock 210 of FIG. 15 and a line, or a suture 250, that may be locked by the line lock 210. The suture 250 is relatively loosely routed through the passageways 222, 224, 228 so that slack is present in the suture 250.

As shown, the suture 250 has a standing portion 252 that may be looped through or around the tissue to be retained. A working portion 254 may be manipulated by a surgeon to control the slack in the standing portion 252. A locking portion 256 separates the working portion 254 from the standing portion 252 and passes through the passageways 222, 224, 228 in the manner illustrated. The locking portion 256 includes a compression section 260 that compresses the working portion 254 against the body 212 when the suture 250 is tightened to prevent motion of the working portion 254 through the working passageway 228.

As shown, the end of the suture 250 adjacent to the standing portion 252 is secured to the line lock 210 via a knot 262. More precisely, the end of the suture 250 has been inserted through the bore 232 of the retention passageway 230 (not visible in FIG. 16), and then the knot 262 has been tied in the end. The knot 262 may be a simple overhand knot. The knot 262 is too large to pass through the bore 232; thus, the end of the suture 250 is effectively secured to the line lock 210.

In this application, the word "secured," with reference to a flexible member, means that some part of the flexible member is connected to an object so as to be inseparable from the object by tension on the flexible member in at least one direction. Thus, even though the knot 262 may be withdrawn from the top surface 214, the fact that the knot 262 is unable to pass through the top surface 214 causes the end of the suture 250 to be "secured" to the line lock 210.

The term "direction," when used in connection with motion of a flexible member such as a line, does not necessarily refer to a static vector. Rather, a "direction" may refer to motion of the line along a pathway, toward one specified end of the pathway. Thus, stating that a line is only able to move along a pathway in one direction means that the line can only be advanced toward one end of the pathway. The line moves along the pathway in one direction even though in the course of advancement along the pathway, segments of the line will simultaneously be moving along a variety of differently-oriented vectors.

The knot 262 may be tied and the suture 250 may be inserted through the bore 232 prior to commencement of the surgical procedure. For example, the knot 262 may be tied and the suture 250 may be inserted through the bore 232 at a manufacturing or packaging facility, prior to packaging of the line lock 210 for shipping. The suture 250 may then be shipped in the same package, preassembled with the line lock 210 and ready for use. A needle (not shown) may similarly be included in the package. Thus, the surgeon need not select and assemble the various components needed to carry out the tissue retention procedure; rather, all necessary parts are already assembled and ready for use prior to commencement of the procedure.

From the end of the locking portion 256 adjacent to the standing portion 252, the locking portion 256 passes through the primary passageway 222, and then extends generally parallel to the groove 236 to define the compression section 260 and reach the secondary passageway 224. From the secondary passageway 224, the locking portion 256 passes through the working passageway 228. The working portion 254 then passes through the space between the compression section 260 and the groove 236.

When tension is applied to the standing portion 252, as when the standing portion 252 is tightened around one or more pieces of tissue, the compression section 260 is drawn taught. The compression section 260 presses the working portion 254 against the groove 236 to keep the working portion 254 from being drawn back through the working passageway 228.

Figure 17:
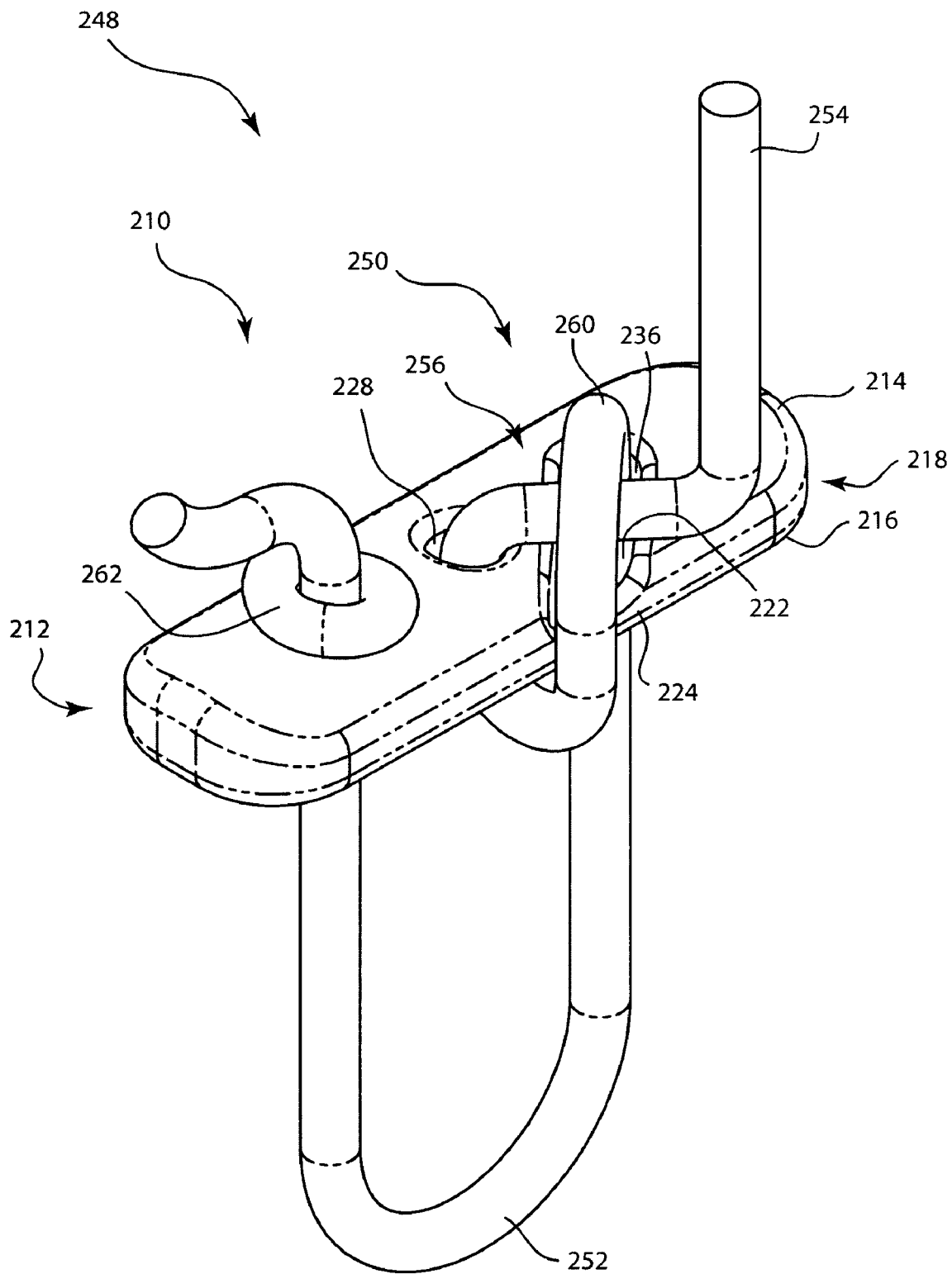
FIG. 17 is a perspective view of the line lock of FIG. 15, with a suture threaded tightly therethrough.

Referring to FIG. 17, a perspective view illustrates the system 248, with the suture 250 routed relatively tightly through the passageways 222, 224, 228 of the line lock 210. As described previously, the compression section 260 presses the working portion 254 against the groove 236 to retain the working portion 254. As the working portion 254 is pressed against the groove 236, bends (not shown) may be formed in the working portion 254 as the working portion 254 conforms to the shape of the groove 236. Such bends enhance locking of the working portion 254 because there is greater friction keeping the working portion 254 in place, and there is no direct path along which tension on the working portion 254 can act to draw the working portion 254 through the space between the compression section 260 and the groove 236. Thus, the locking portion 256 cooperates with the knot 262 to retain both ends of the standing portion 252, thereby enabling the standing portion 252 to securely retain tissue.

Figure 18:
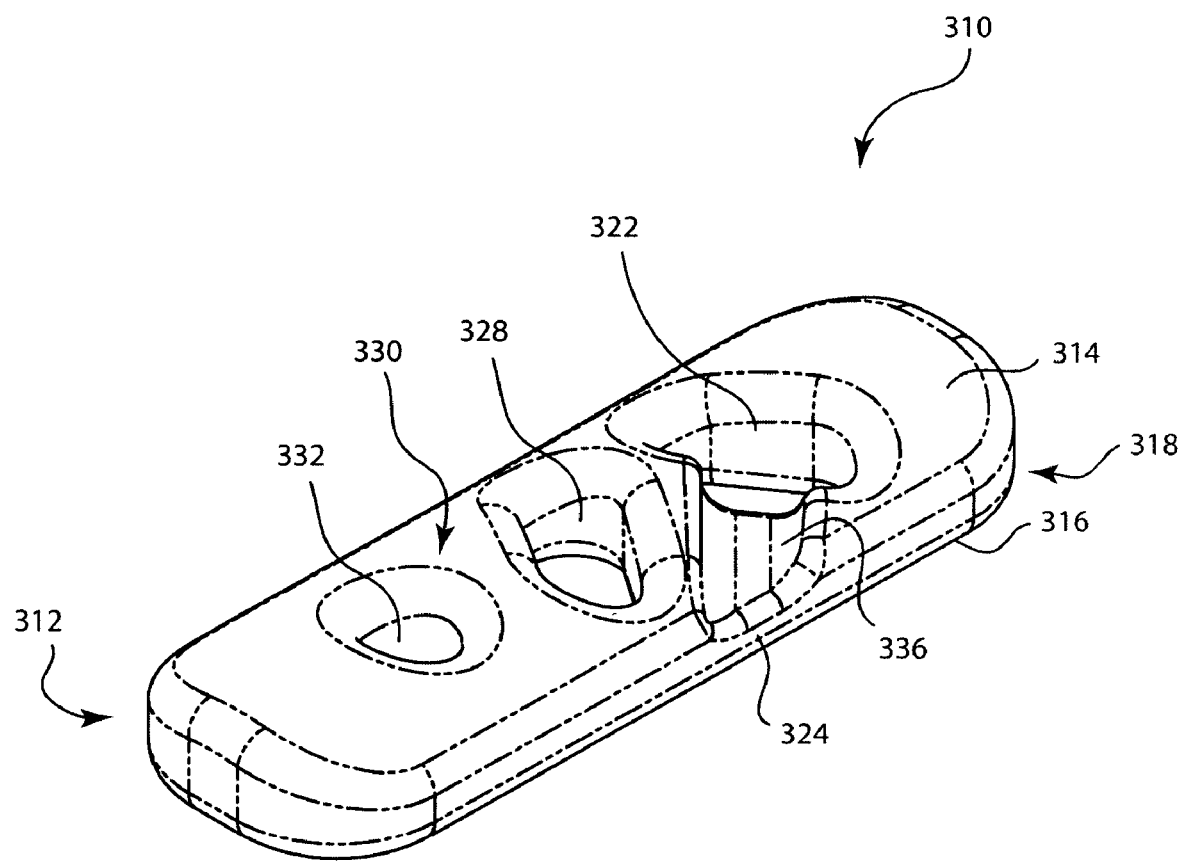
FIG. 18 is a perspective view of a line lock according to yet another embodiment of the invention.

Referring to FIG. 18, a perspective view illustrates a line lock 310 according to another alternative embodiment of the invention. The line lock 310 has a body 312 with a generally rectangular shape, with a top surface 314, a bottom surface 316, and a periphery 318 that separates the top surface 314 from the bottom surface 316. The body 312 fully bounds a primary passageway 322 and partially bounds a secondary passageway 324. As in the previous embodiment, the secondary passageway 324 is defined by a portion of the periphery 318 of the body 312.

The body 312 also fully bounds a working passageway 328 and a retention passageway 330. The retention passageway 330 has a bore 332 positioned to retain a loop of a suture (not shown in FIG. 18). The body 312 further defines a groove 336 extending between the primary and secondary passageways 322, 324. The primary passageway 222, the working passageway 228, and the groove 336 may all be somewhat wider than their counterparts of the previous embodiment to permit two suture portions to be simultaneously routed therethrough. The operation of the various passageways 322, 324, 328, 330 and the groove 336 will be described in connection with FIGS. 19 and 20.

Figure 19:
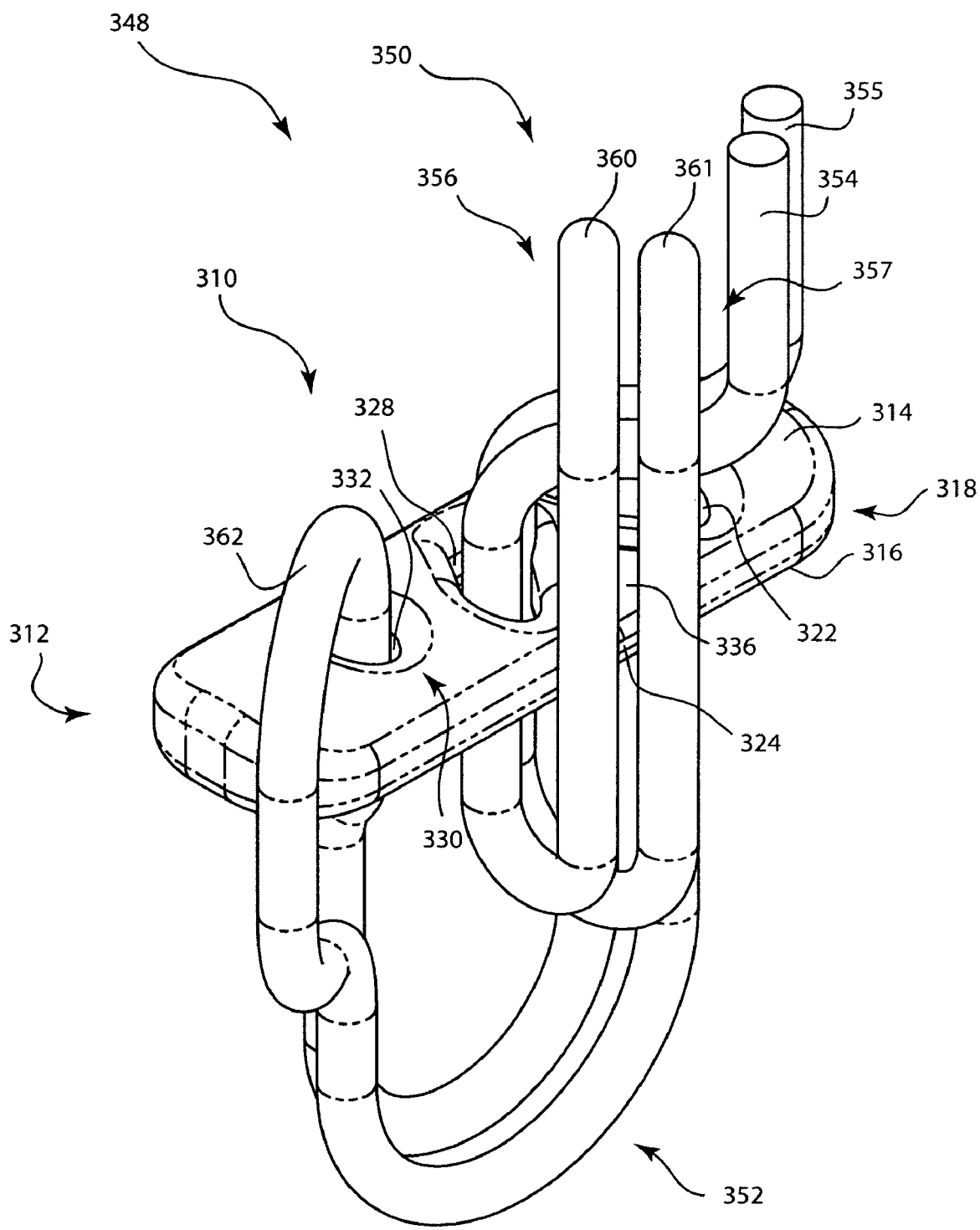
FIG. 19 is a perspective view of the line lock of FIG. 18, with the suture threaded loosely therethrough.

Referring to FIG. 19, a perspective view illustrates a system 348 including the line lock 310 of FIG. 18 and a line, or a suture 350, which may be locked by the line lock 310. The suture 350 is relatively loosely routed through the passageways 322, 324, 328 so that slack is present in the suture 350.

As shown, the suture 350 has a standing portion 352 with two separate strands, each of which may be looped through or around the tissue to be retained. First and second working portions 354, 355 may be manipulated by a surgeon to control the slack in the standing portion 352. First and second locking portions 356, 357, respectively, separate the first and second working portions 354, 355, respectively, from the standing portion 352. The locking portions 356, 357 pass through the passageways 322, 324, 328 side-by-side, in the manner illustrated.

The first locking portion 356 includes a first compression section 360 that compresses the first and second working portions 354, 355 against the body 312 when the suture 350 is tightened to prevent motion of the first working portion 354 through the working passageway 328. Similarly, the second locking portion 357 includes a second compression section 361 that compresses the first and second working portions 354, 355 against the body 312 when the suture 350 is tightened to prevent motion of the second working portion 355 through the working passageway 328.

The suture 350 also has a loop 362 that passes through the bore 332 of the retention passageway 330. The loop 362 effectively secures the two strands of the working portion 352 to the line lock 310, just as the knot 262 of the previous embodiment secured the single strand of the working portion 252 to the line lock 210. As with the knot 262, the loop 362 may be inserted through the bore 332 prior to commencement of the surgical procedure. For example, the loop 362 may be inserted through the bore 332 at a manufacturing or packaging facility, prior to packaging of the line lock 310 for shipping such that the suture 350 is shipped pre-attached to the line lock 310. A needle (not shown) may similarly be included in the package.

The first and second locking portions 356, 357 extend along a pathway similar to that followed by the locking portion 256 of the previous embodiment. Accordingly, when the standing portion 352 is drawn taught, the first and second compression sections 360, 361 press the first and second working portions 354, 355 against the groove 336 to keep the working portions 354, 355 from moving back through the working passageway 328.

Figure 20:
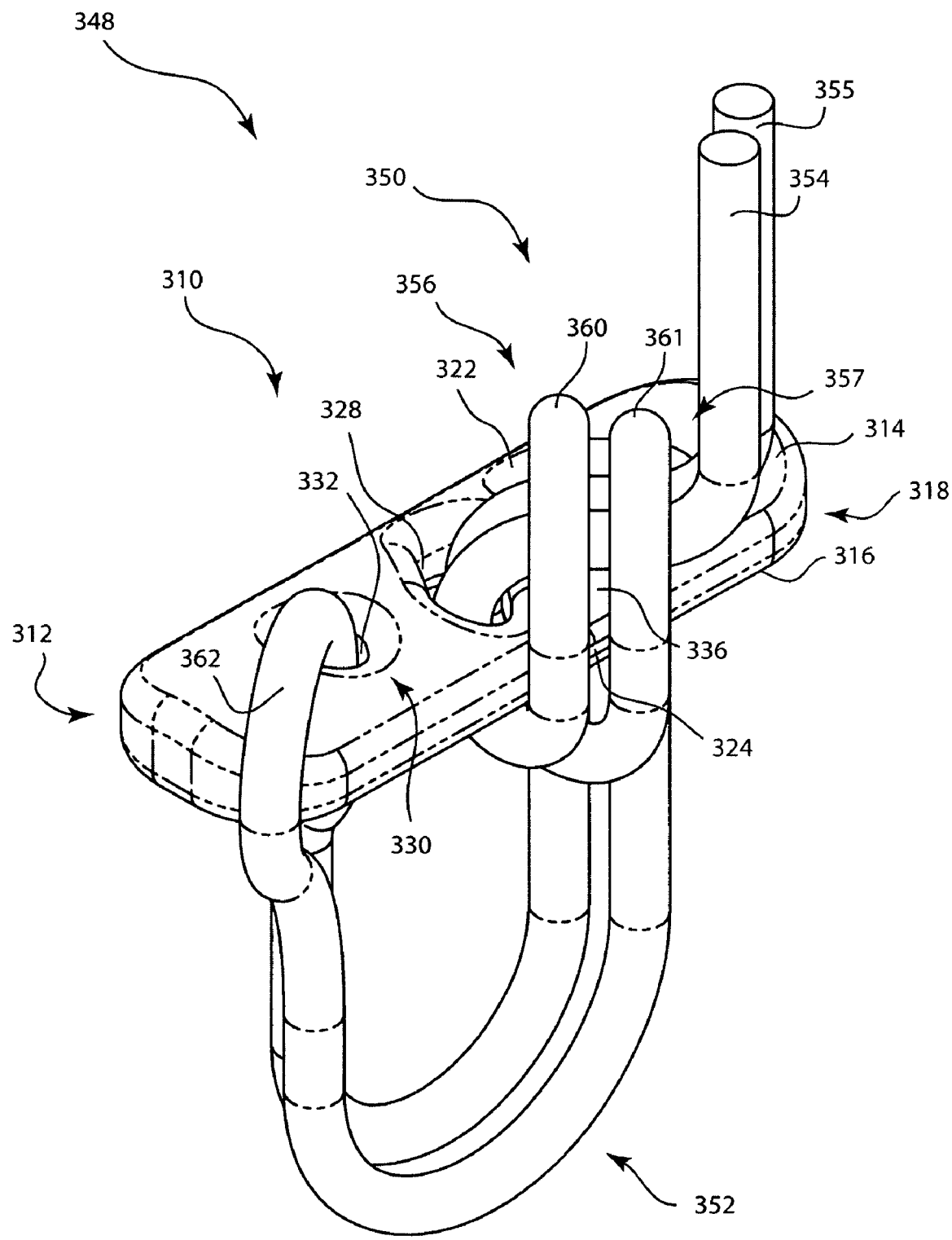
FIG. 20 is a perspective view of the line lock of FIG. 18, with the suture threaded tightly therethrough.

Referring to FIG. 20, a perspective view illustrates the system 348, with the suture 350 routed relatively tightly through the passageways 322, 324, 328 of the line lock 310. As described previously, the compression sections 360, 361 press the working portions 354, 355 against the groove 336 to retain the working portions 354, 355. Bends (not shown) may be formed in the working portions 354, 355 as the working portions 354, 355 conform to the shape of the groove 336 to enhance locking of the working portions 354, 355. Thus, the locking portions 356, 357 cooperate with the loop 362 to retain both ends of the standing portion 352, thereby enabling the standing portion 352 to securely retain tissue.

As mentioned previously, it may be desirable to package the line lock 190 in a cartridge that facilitates threading of the line 100 through the passageways 158, 160, 162. One example of such a cartridge is illustrated in FIGS. 21 through 25, and is shown with respect to the line lock 190 of FIGS. 14A and 14B. However, those of skill in the art will recognize that a similar cartridge may be provided for a line lock according to any other embodiment of the invention, such as the line locks 210, 310 of FIGS. 15-20.

Figure 21:
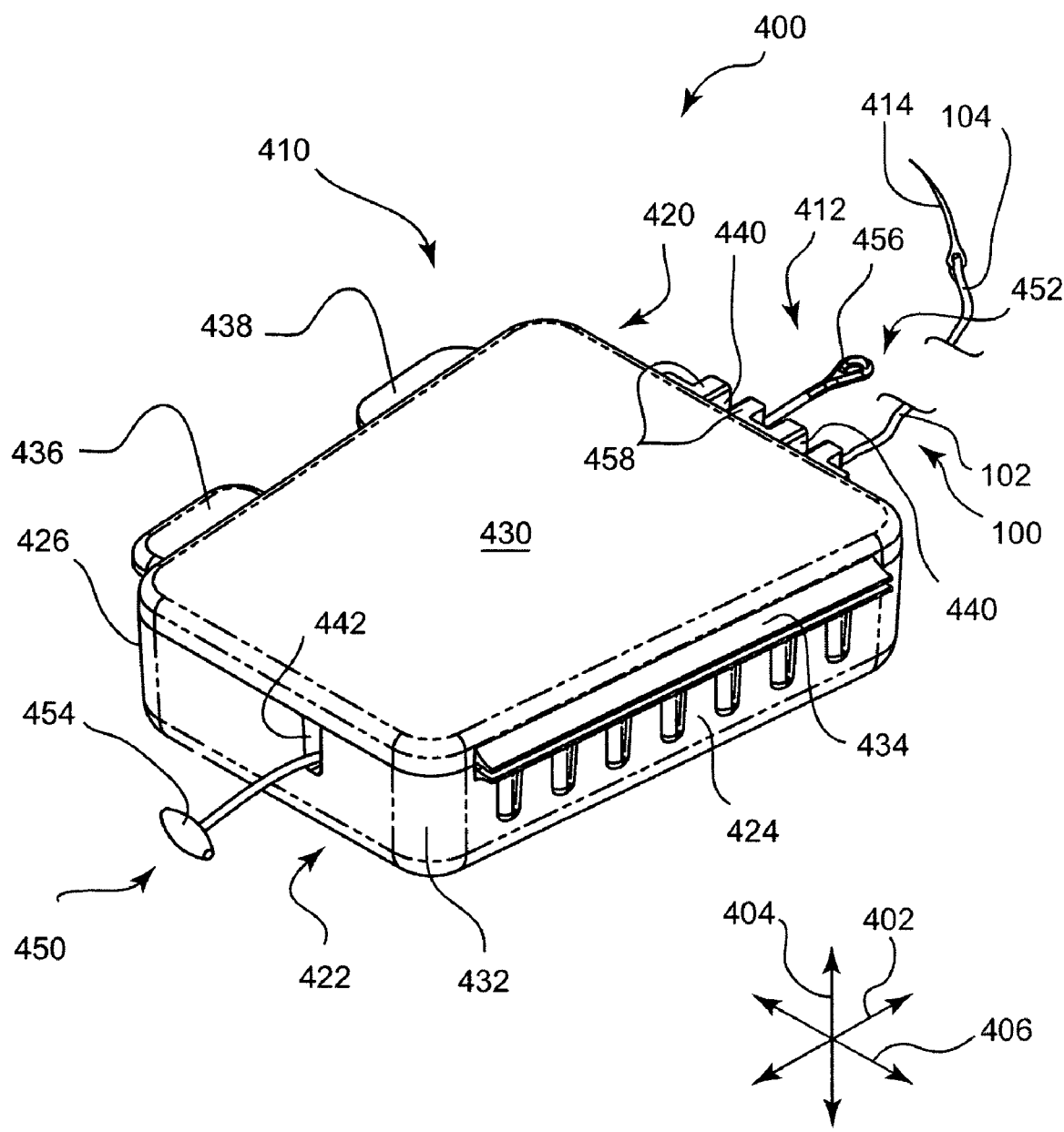
FIG. 21 is a perspective view of a system including a cartridge with a threader that facilitates the insertion of the pre-attached suture through the passageways of the line lock of FIGS. 14A and 14B.

Referring to FIG. 21, a perspective view illustrates one embodiment of a system 400 including the line lock 190 of FIGS. 14A and 14B (not visible in FIG. 21), and various implements to help insert, or "thread," the line 100 through the passageways 158, 160, 162 of the line lock 190. A longitudinal direction 402, a lateral direction 404, and a transverse direction 406 cooperate to form a system of orthogonal axes that will be used for reference in the following description.

In addition to the line lock 190, the system 400 includes a cartridge 410, a threader 412, and a needle 414. The cartridge 410 contains the line lock 190 and, when in the closed configuration shown in FIG. 21, substantially encloses the line lock 190 to facilitate insertion of the line 100 through the passageways 158, 160, 162, and possibly, to help isolate the line lock 190 from contaminants. In this application, the phrase "substantially enclose" does not require full enclosure; rather, some portion(s) of the substantially enclosed part may protrude from the enclosure.

The cartridge 410 may be formed of a plastic such as polypropylene, PEEK, or the like. The threader 412 passes through the cartridge 410 along a pathway to enable a user to draw the line 100 through the passageways 158, 160, 162 along the correct pattern, as will be described in greater detail subsequently. The threader 412 may be formed substantially of a fibrous material or a plastic, such as nylon.

The needle 414 is attached to the working end 104 of the line 100, for example, by knotting, ultrasonic welding, swaging, or the like. The needle 414 may be attached to the working end 104 prior to packaging of the system 400 for shipping. Thus, the surgeon need not locate and attach an appropriate needle to the line 100 prior to surgical use. The needle 414 may be any of a variety types suitable for surgical use.

As shown in FIG. 21, the cartridge 410 has a first longitudinal end 420, a second longitudinal end 422, a first lateral end 424, and a second lateral end 426. The threader 412 passes through the longitudinal ends 420, 422. Furthermore, the cartridge 410 has a lid 430 designed to move with respect to the remainder of the cartridge 410, which will be referred to as a containment portion 432. More specifically, a living hinge 434 extends generally along the first lateral end 424, between the adjacent edges of the lid 430 and the containment portion 432. The living hinge 434 is integrally formed with the lid 430 and the containment portion 432 and flexes to enable pivotal motion of the lid 430 with respect to the containment portion 432. In alternative embodiments, a conventional hinge may be used, or a lid may be slidable with respect to and/or fully removable from the remainder of the cartridge, thereby obviating the need for a hinging mechanism.

A first tab 436 integrally formed with the lid 430 and a second tab 438 integrally formed with the containment portion 432 may easily be pushed in opposite directions, for example, by a user's thumbs, to open the cartridge 410. The lid 430 and the containment portion 432 may be designed to adhere to each other at the second lateral end 426 so that the cartridge 410 only opens when a threshold force is applied. Thus, the cartridge 410 may not open if dropped or jostled.

The first longitudinal end 420 has a first set of slots 440 through which the threader 412 and the line 100 pass. More precisely, the threader 412 passes through one slot of the first set of slots 440. From the end 192, the standing portion 102 of the line 100 extends out of the cartridge 410 through the other of the first set of slots 440.

Similarly, the second longitudinal end 422 has a slot 442 through which the threader 412 passes. Thus, the threader 412 extends into the cartridge 410 through the first longitudinal end 420 and out again through the second longitudinal end 422. The threader 412 has a leading end 450 adjacent to the second slot 442 and a trailing end 452 adjacent to the first set of slots 440.

The leading end 450 has a pull feature designed to facilitate grasping and drawing of the leading end 450 by hand. In the embodiment of FIG. 21, the pull feature takes the form of a grip 454 that may be easily grasped, for example, between a thumb and an index finger. The grip 454 may be a plastic rod crimped, insert molded, adhesive bonded, or otherwise attached to the remainder of the threader 412. In alternative embodiments, one or more differently configured pull features may be used, including rigid rings, flexible loops, spherical beads, squared beads, and the like.

Additionally, the trailing end 452 has a suture retention feature designed to retain a portion of the line 100 to enable the threader 412 to draw the line 100 through the passageways 158, 160, 162 of the line lock 190. In FIG. 21, the suture retention feature takes the form of an eyelet 456, which is able to receive an end of the line 100 such that the end can double back on itself to be drawn through the cartridge 410. The eyelet 456 may be crimped, adhesive bonded, insert molded, or otherwise attached to the remainder of the threader 412. In alternative embodiments, one or more differently configured suture retention features may be used, including adhesive-coated surfaces, collets, clips, flexible loops, and the like.

The eyelet 456 may be retained to ensure that it is not drawn into the cartridge 410 prior to attachment to the line 100. For example, the containment portion 432 may have retention posts 458 that extend in the longitudinal direction 402 on either side of the slots of the first set of slots 440 through which the threader 412 passes. The eyelet 456 may optionally be looped around the retention posts 458 so that the eyelet 456 is unable to enter the corresponding slot of the first set of slots 440 until the eyelet 456 is removed from around the retention posts 458. The eyelet 456 may need to be slightly larger than shown in FIG. 21 to enable it to encircle a pair of the retention posts 458. The retention posts 458 may also serve a similar function if a loop or other flexible suture retention feature is used in place of the eyelet 456.

Figure 22:
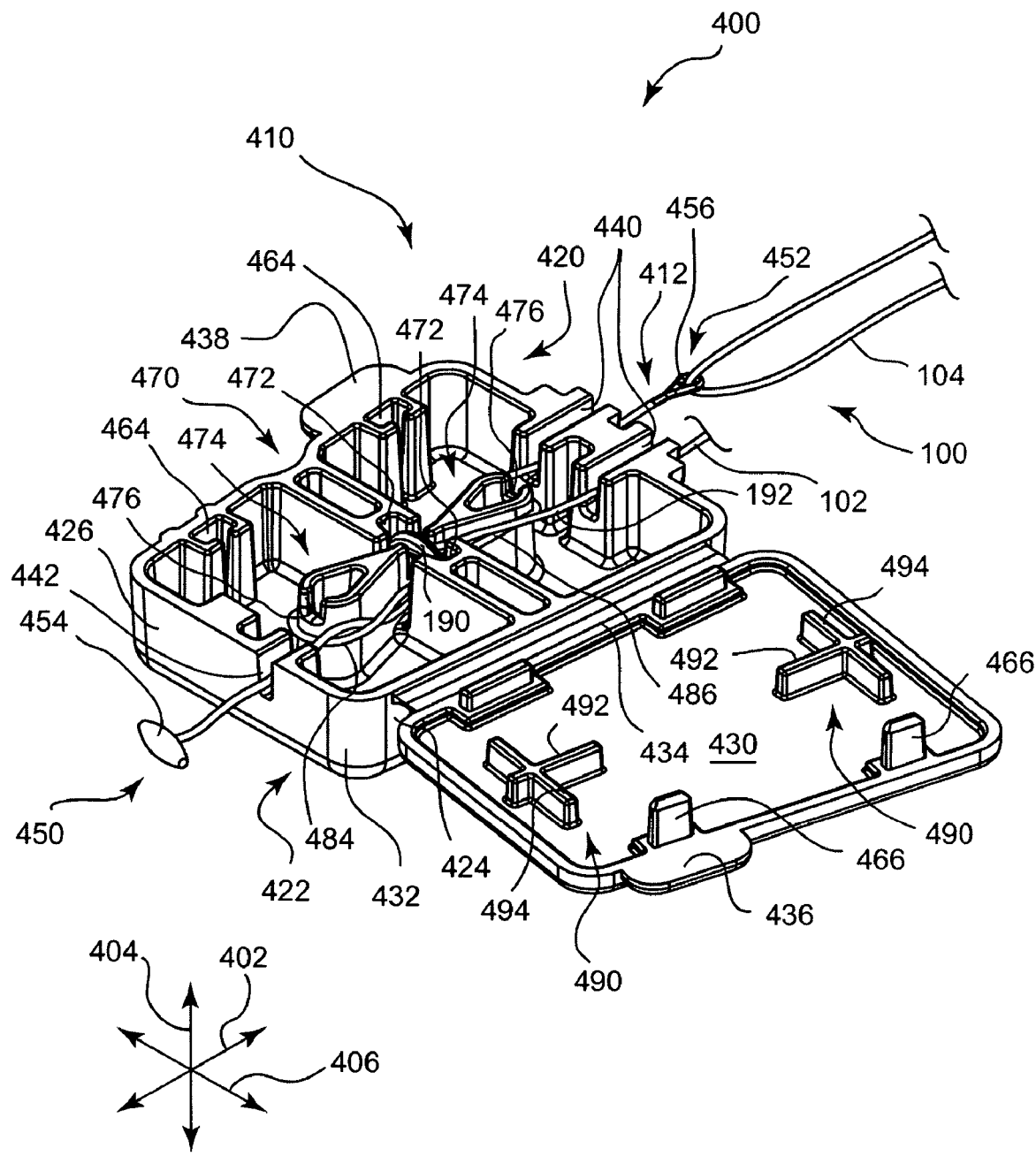
FIG. 22 is a perspective view of the system of FIG. 21, with the lid of the cartridge open and the suture coupled to the trailing end of the threader.

Referring to FIG. 22, a perspective view illustrates the system 400 of FIG. 21, with the cartridge 410 in the open configuration to expose the line lock 190. The line 100 has also been inserted into engagement with the trailing end 452 of the threader 412. More precisely, the needle 414 and the working portion 104 have already been inserted through or around the tissue or tissues to be retained, and the needle 414 has been removed from the working portion 104. The working portion 104 has then been inserted through the eyelet 456 of the threader 412. The working portion 104 is doubled back on itself to permit the eyelet 456 to draw it through the cartridge 410 and through the passageways 158, 160, 162 (not visible in FIG. 22) of the line lock 190.

In alternative embodiments, multiple sutures or ends may need to be inserted through passageways of a line lock, such as the line lock 310 of FIGS. 18 through 20. A cartridge (not shown) for such an embodiment may have multiple threaders, each of which is positioned to draw one suture or one end through the corresponding passageways. Operation of such a cartridge may otherwise be similar to that of the cartridge 410.

Returning to FIG. 22, the containment portion 432 has a pair of sockets 464 formed therein. Each of the sockets 464 may provide a generally rectangular cavity surrounded by a wall that is slotted to permit expansion of the socket 464. The lid 430 has a pair of posts 466 that are generally rectangular in shape, and are sized and positioned to slide into the sockets 464 when the cartridge 410 is in the closed configuration. The posts 466 may be sized to fit relatively tightly into the sockets 464 so that the cartridge 410 does not open until the threshold force is applied to remove the posts 466 from the sockets 464.

The containment portion 432 also has a central divider 470 that extends generally along the lateral direction 404 to effectively separate the containment portion 432 into two separate compartments. The containment portion 432 defines a retention feature designed to retain the line lock 190. In this application, the terms "retention feature" and "threading feature" are to be broadly interpreted to include, not just single structural elements, but also groups of elements that cooperate to carry out line lock retention or suture threading.

In FIG. 22, the retention feature takes the form of a pair of troughs 472 positioned on either side of a space in which the line lock 190 rests within the containment portion 432. The troughs 472 face each other such that they retain the line lock 190 to resist motion of the line lock 190 along the longitudinal and lateral directions 402, 404. The troughs 472 are exposed on the open side of the containment portion 432 so that the line lock 190 can be inserted into the space between the troughs 472, or removed therefrom, by moving the line lock 190 along the transverse direction 406.

Additionally, the containment portion 432 has a threading feature designed to help guide the line 100 through the passageways 158, 160, 162 along the desired pattern. In FIG. 22, the threading feature takes the form of a pair of posts 474 positioned on either side of the central divider 470, and thus on either side of the space in which the line lock 190 rests. Each of the posts 474 may have a generally teardrop-shaped cross section, as taken through a plane parallel to the longitudinal and lateral directions 402, 404. Each of the posts 474 also has a slot 476 facing the adjacent one of the first and second longitudinal ends 420, 422.

The threader 412 is wrapped around the posts 474 along a configuration similar to that provided by the line 100 illustrated in FIGS. 14A and 14B. More precisely, from its trailing end 452, the threader 412 passes through one of the first set of slots 440, then through the primary passageway 158 (not visible in FIG. 22) and then through the secondary passageway 160 (not visible) to define a first loop 484 of the threader 412. From the secondary passageway 160, the threader 412 passes through the working passageway 162 (not visible) to define a second loop 486 of the first threader 412. From the working passageway 162, the threader 412 extends through the first loop 484 and then passes through the second slot 442, to the leading end 450.

The various portions of the threader 412 may be positioned to correspond to portions of the line 100, as labeled in FIGS. 14A and 14B. For example, the trailing end 452 may correspond to the standing portion 102 of the line 100, the leading end 450 may correspond to the working portion 104, and the loops 484, 486 may correspond to the locking portion 106. The first loop 484 of the threader 412 may more precisely correspond to the compression section 110 of the locking portions 106. Accordingly, when the line 100 is drawn through the passageways 158, 160, 162 by the threader 412, the line 100 assumes a configuration having the various portions 102, 104, 106, as illustrated in FIGS. 14A and 14B.

As also shown in FIG. 22, the lid 430 has a pair of blocking members 490 that engage the posts 474 when the cartridge 410 is closed to keep the first and second loops 484, 486 in place. More precisely, each of the blocking members 490 has a longitudinal portion 492 extending along the longitudinal direction 402, and a lateral portion 494 extending along the lateral direction 404. The longitudinal portions 492 may be positioned to seat in the slots 476 of the posts 474 to ensure that the loops 484, 486 cannot slip from the posts 474 by moving transversely toward the lid 430, into a gap that may exist between the posts 474 and the lid 430. Similarly, the lateral portions 494 may be positioned inward of and adjacent to the first set of slots 440 and to the second slot 442 to ensure that the leading and trailing ends 450, 452 of the threader 412 are unable to slide out of the slots 440, 442 by moving transversely toward the lid 430, into a gap that may exist between the slots 440, 442 and the lid 430.

Figure 23:
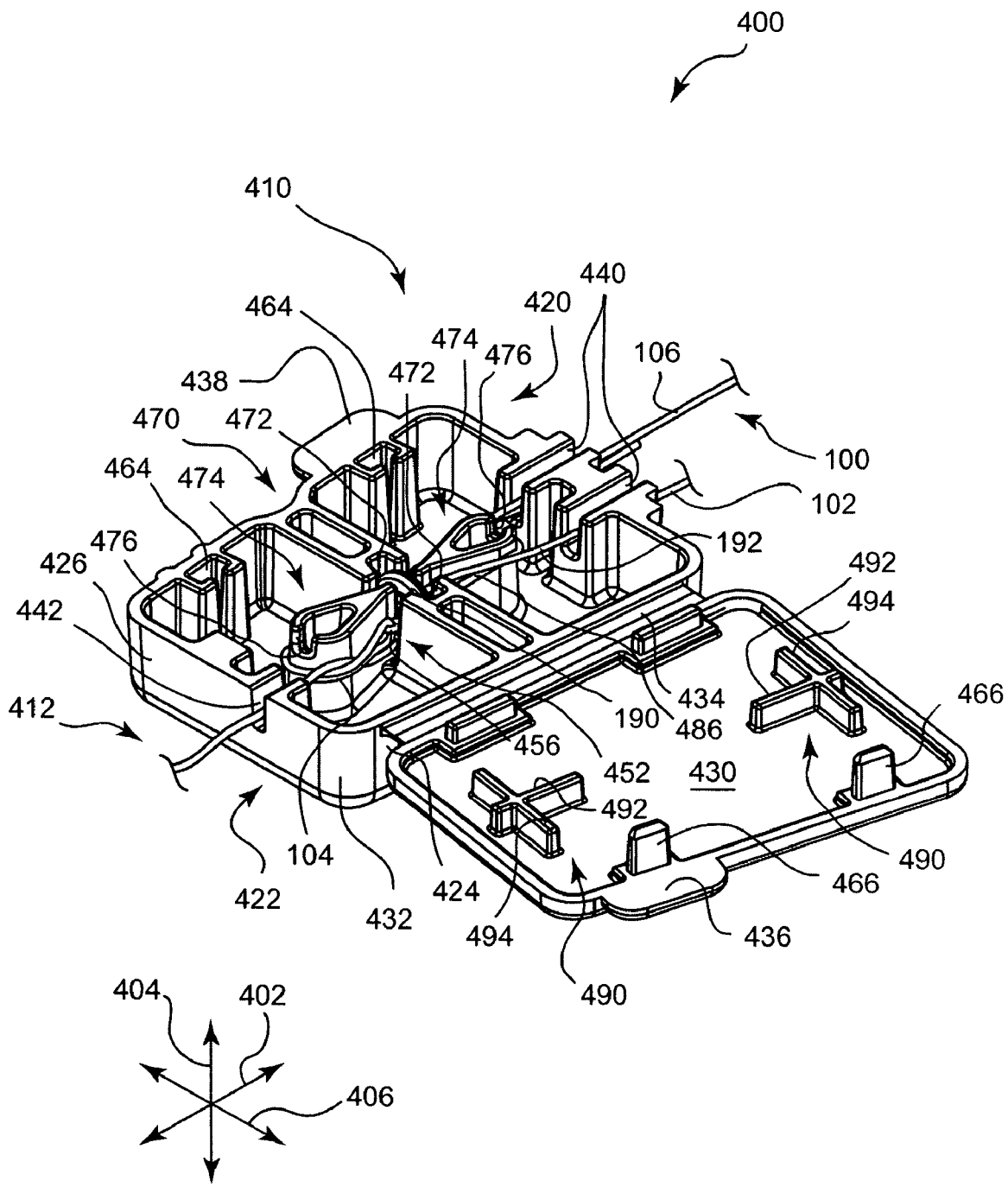
FIG. 23 is a perspective view of the system of FIG. 21, with the cartridge open and the suture drawn part-way through the cartridge.

Referring to FIG. 23, a perspective view illustrates the system 400 of FIG. 23, with the cartridge 410 open to expose the line lock 190. In FIG. 23, the threader 412 is drawn partially through the cartridge 410 so that the working portion 104 of the line 100 is drawn partially along the pathway followed by the threader 412. More precisely, the working portion 104 has been drawn through the corresponding one of the first set of slots 420 and through the primary passageway 158 (not visible in FIG. 23) of the line lock 190. Further, the working portion 104 has been drawn along the first loop 484 of the threader 412 so that the working portion 104 encircles the post 474 toward the second longitudinal side 422, in place of the first loop 484.

The leading, doubled-over portion of the working portion 104 is thus poised to enter the secondary passageway 160 (not visible). From the secondary passageway 160, the working portion 104 will then be drawn along the second loop 486 of the threader 412, through the working passageway 162 (not visible), and then through the second slot 442 in the second longitudinal end 422. The leading, doubled-over portion of the working portion 104 will then protrude from the cartridge 410 and may easily be grasped and drawn by hand until the line lock 190 is positioned at the desired location along the length of the line 100.

The line 100 may be drawn through the cartridge 410 with the cartridge in the open configuration, as illustrated in FIG. 23, or with the cartridge 410 in the closed configuration. If desired, part or all of the cartridge 410 may be made translucent or transparent so that a user can easily verify proper threading without opening the cartridge 410.

Figure 24:
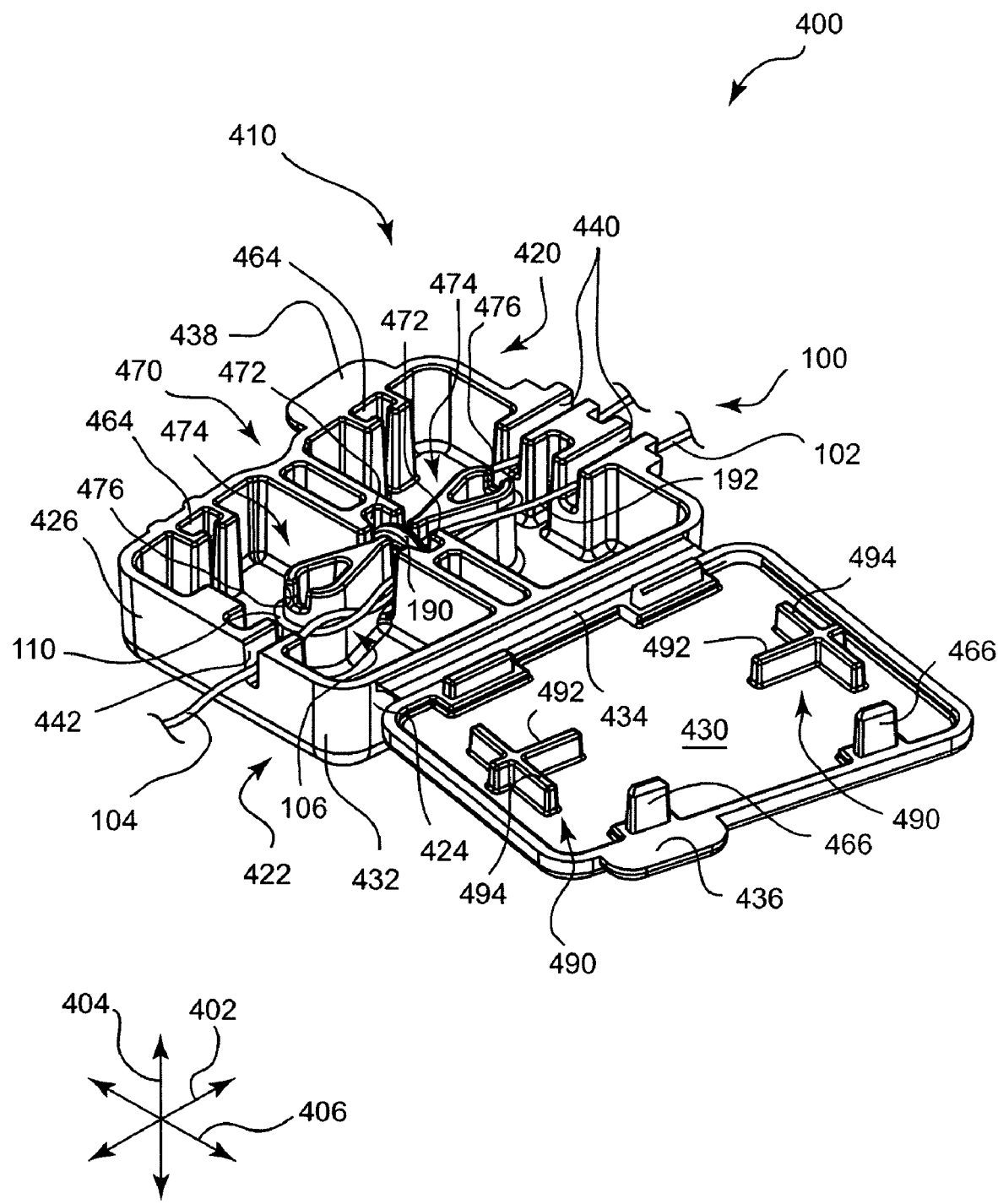
FIG. 24 is a perspective view of the system of FIG. 21, with the cartridge open and the suture fully drawn through the cartridge to pass through the passageways of the line lock.

Referring to FIG. 24, a perspective view illustrates the system 400 of FIG. 21, with the cartridge 410 in the open configuration to expose the line lock 190. The line 100 has been fully threaded through the passageways 158, 160, 162 of the line lock 190 in the manner illustrated in FIGS. 14A and 14B. Accordingly, the line lock 190 need only be removed from the cartridge 410 prior to use to retain tissue.

Figure 25:
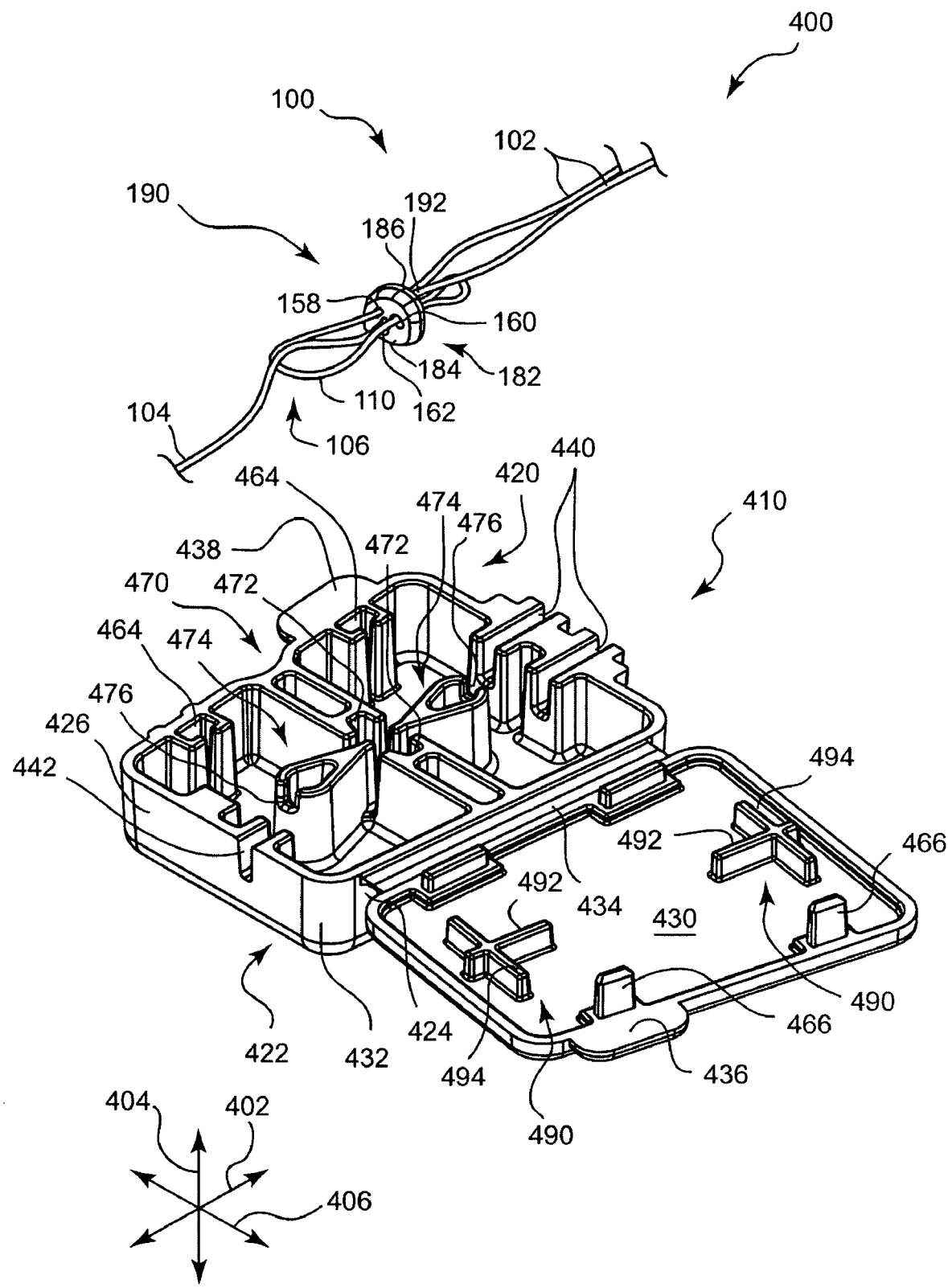
FIG. 25 is a perspective view of the system of FIG. 21, with the cartridge open and the suture and line lock removed from the cartridge for use.

Referring to FIG. 25, a perspective view illustrates the system 400 of FIG. 21, with the cartridge 410 in the open configuration, and with the line lock 190 and the line 100 removed from the cartridge 410 for use. The line lock 190 has been drawn from the space between the troughs 472 by drawing the line lock 190 along the transverse direction 406, toward the space the lid 430 would occupy if the cartridge 410 were closed. The line 100 is also drawn along the same direction to slide free of the posts 474 and the slots 440, 442.

As shown, the various portions and sections 102, 104, 106, 110 of the line 100 are arranged substantially as shown in FIGS. 14A and 14B. The standing portion 102 may be inserted through an anchor embedded in tissue, or otherwise positioned behind tissues to be retained by the system 400, prior to performance of the threading process set forth above. If the standing portion 102 is not required to pass through an enclosed aperture, the standing portion 102 may be positioned with respect to the tissue to be retained after the line 100 has been threaded through the line lock 190.

Once the line 100 has been properly threaded through the passageways 158, 160, 162, the line lock 190 may then be used to retain the tissue as desired. This may be accomplished by following the procedures outlined previously, i.e., holding the working portion 104 and advancing the line lock 190 along the line 100 to constrict the standing portion 102, either with or without an insertion tool, and then trimming the line 100 to the desired length.

Thus, the line 100 may easily be threaded through the line lock 190 in the proper pattern to ensure that the line lock 190 is able to perform as desired. Threading may be performed without significantly compromising the sterility of the line lock 190, the line 100, or the operating environment. Thus, the convenience, reliability, and safety of tissue retention operations may be enhanced through the present invention.

The present invention has particular relevance to surgery, and more particularly to tissue retention through the use of sutures. However, the principles, structures, and methods of the present invention may also be extended to other fields, including the use of larger line locks for locking ropes or cables in a wide variety of applications.

The present invention may be embodied in other specific forms without departing from its spirit or essential characteristics. For example, above are described various alternative examples of different adjustable line locks. It is appreciated that various features of the line locks can be mixed and matched to form a variety of other alternatives, each of which may have a different threading system according to the invention. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for retaining tissue, the system comprising:
a line lock comprising a body at least partially bounding a plurality of passageways; and
a suture comprising a first end secured to the body and a locking portion spaced apart from the first end;
wherein the passageways are shaped and arranged to cooperate to receive the locking portion;
wherein the suture is routed through the passageways such that the locking portion of the suture is able to be drawn along a pathway through at least some of the passageways fully bounded by the body, along only one direction along the pathway defined by the routing of the suture, wherein the locking portion is movable through the passageways such that a compression section of the locking portion presses another part of the locking portion against the line lock in response to tension urging the locking portion to move through the passageways opposite to the one direction, and the line lock is held in place relative to the suture when the part of the locking portion is pressed against the line lock.

2. The system of claim 1, wherein the first end is substantially permanently secured to the body.

3. The system of claim 1, wherein the passageways comprise a retention passageway having a bore within which the first end is retained.

4. The system of claim 3, wherein the first end extends through the bore, the first end comprising a knot sized to prevent passage of the knot through the bore.

5. The system of claim 3, wherein the first end is insert molded into the bore.

6. The system of claim 3, wherein the first end is bonded in place with respect to the bore by an adhesive applied between the first end and the bore.

7. The system of claim 1, wherein the passageways comprise a primary passageway and a secondary passageway, wherein the passageways cooperate to receive the locking portion along a pathway extending through the primary passageway, then the secondary passageway, such that the locking portion is able to be drawn along the pathway toward the secondary passageway, but not toward the primary passageway.

8. The system of claim 7, wherein the primary and secondary passageways cooperate to receive the locking portion, thereby defining the compression section extending between the primary and secondary passageways to press a working portion of the suture against the body.

9. The system of claim 8, wherein the passageways further comprise a working passageway through which the locking portion passes, wherein the working portion extends from the working passageway between the compression section and the body.

10. The system of claim 8, wherein each of the passageways is fully bounded by the body.

11. The system of claim 8, wherein at least one of the passageways comprises a notch contiguous with a periphery of the body, the periphery extending generally perpendicular to at least one of the passageways.

12. The system of claim 8, wherein the body further comprises a groove positioned proximate the primary and secondary passageways such that, in response to tension on the locking portion, the working portion is pressed against the groove along an orientation nonparallel to the groove to enhance retention of the locking portion by the line lock.

13. The system of claim 7, further comprising a cartridge comprising a retention feature shaped to retain the line lock, and a threading feature shaped to facilitate insertion of the locking portion through the passageways.

14. The system of claim 13, wherein the cartridge is shaped to substantially enclose the line lock, wherein the cartridge further comprises a lid that is movable with respect to a remainder of the cartridge to open the cartridge to permit removal of the line lock from the cartridge.

15. The system of claim 13, wherein the retention feature comprises a pair of troughs positioned on either side of a space into which the line lock fits, wherein the troughs are shaped to restrict motion of the line lock along two perpendicular axes.

16. The system of claim 15, wherein the threading feature comprises a pair of posts positioned on either side of the space such that the suture can move around and between the posts to move through the passageways along a pathway.

17. The system of claim 13, further comprising a threader routed through the passageways along the pathway via at least partial encirclement of the threading feature such that the threader is drawable to draw the locking portion through the passageways along the pathway.

18. The system of claim 13, further comprising a needle secured to a second opposing end of the suture, wherein the locking portion extends between the first and second ends.

19. A system for retaining tissue, the system comprising:
a line lock comprising a body at least partially bounding a plurality of passageways; and
a suture comprising a first end substantially permanently secured to the body and a locking portion spaced apart from the first end;
wherein the passageways are shaped and arranged to receive the locking portions;
wherein the suture is routed through the passageways such that the locking portion of the suture is able to be drawn along a pathway through at least some of the passageways fully bounded by the body, along only one direction along the pathway defined by the routing of the suture, wherein the locking portion is movable through the passageways such that a compression section of the locking portion presses another part of the locking portion against the line lock in response to tension urging the locking portion to move through the passageways opposite to the one direction, and the line lock is held in place relative to the suture when the part of the locking portion is pressed against the line lock.

20. The system of claim 19, wherein the passageways comprise a retention passageway having a bore within which the first end is retained.

21. The system of claim 20, wherein the first end is retained in the bore via an attachment mechanism selected from the group consisting of a knot formed in the first end, insert molding of the first end into the bore, and adhesive bonding of the first end into the bore.

22. The system of claim 19, wherein the passageways comprise a primary passageway and a secondary passageway, wherein the passageways cooperate to receive the locking portion along a pathway extending through the primary passageway, then the secondary passageway, such that the locking portion is able to be drawn along the pathway toward the secondary passageway, but not toward the primary passageway.

23. The system of claim 22, wherein the primary and secondary passageways cooperate to receive the locking portion, thereby defining the compression section extending between the primary and secondary passageways to press a working portion of the suture against the body.

24. The system of claim 23, wherein the passageways further comprise a working passageway through which the locking portion passes, wherein the working portion extends from the working passageway between the compression section and the body.

25. The system of claim 23, wherein each of the passageways is fully bounded by the body.

26. The system of claim 23, wherein at least one of the passageways comprises a notch contiguous with a periphery of the body, the periphery extending generally perpendicular to at least one of the passageways.

27. The system of claim 23, wherein the body further comprises a groove positioned proximate the primary and secondary passageways such that, in response to tension on the locking portion, the working portion is pressed against the groove along an orientation nonparallel to the groove to enhance retention of the locking portion by the line lock.

28. The system of claim 22, further comprising a cartridge comprising a retention feature shaped to retain the line lock, and a threading feature shaped to facilitate insertion of the locking portion through the passageways.

29. The system of claim 28, further comprising a threader routed through the passageways along a pathway via at least partial encirclement of the threading feature such that the threader is drawable to draw the locking portion through the passageways along the pathway.

30. The system of claim 28, further comprising a needle secured to a second opposing end of the suture, wherein the locking portion extends between the first and second ends.

31. A system for retaining tissue, the system comprising:
a line lock comprising a body at least partially bounding a plurality of passageways including a retention passageway; and
a suture comprising a standing portion looped through the retention passageway, a first locking portion, and a second locking portion, wherein the first and second locking portions are adjacent to either end of the standing portion;
wherein the passageways are shaped and arranged to cooperate to receive the first and second locking portions such that each of the first and second locking portions is able to be drawn through the passageways along only one direction along a pathway defined by the routing of the suture, wherein the first and second locking portions are movable through the passageways such that first and second compression sections of the first and second locking portions press parts of the first and second locking portions against the line lock in response to tension urging the first and second locking portions to move through the passageways opposite to the one direction, and the line lock is held in place relative to the suture when the parts of the first and second locking portions are pressed against the line lock.

32. The system of claim 31, wherein the first and second locking portions follow substantially the same pathway through the passageways.

33. The system of claim 32, wherein the passageways further comprise a primary passageway and a secondary passageway, wherein the pathway extends through the primary passageway, then the secondary passageway, such that the locking portion is able to be drawn along the pathway toward the secondary passageway, but not toward the primary passageway.

34. The system of claim 33, wherein the primary and secondary passageways cooperate to receive each of the first and second locking portions, thereby defining the first and second compression sections extending between the primary and secondary passageways to press first and second working portions of the suture against the body.

35. The system of claim 34, wherein the passageways further comprise a working passageway through which the first and second locking portions pass, wherein the first and second working portions extend from the working passageway between the first and second compression sections, respectively, and the body.

36. The system of claim 34, wherein at least one of the passageways comprises a notch contiguous with a periphery of the body, the periphery extending generally perpendicular to at least one of the passageways.

37. The system of claim 34, wherein the body further comprises a groove positioned proximate the primary and secondary passageways such that, in response to tension on at least one of the first and second locking portions, at least one of the first and second working portions is pressed against the groove along an orientation nonparallel to the groove to enhance retention of the at least one of the first and second locking portions by the line lock.

38. The system of claim 32, further comprising a cartridge comprising a retention feature shaped to retain the line lock, and a threading feature shaped to facilitate insertion of the locking portion through the passageways.

39. The system of claim 38, further comprising a threader routed through the passageways along the pathway via at least partial encirclement of the threading feature such that the threader is drawable to draw the locking portion through the passageways along the pathway.

* * * * *

UNITED STATES PATENT AND TRADEMARK OFFICE
CERTIFICATE OF CORRECTION

PATENT NO. : 7,594,923 B2  Page 1 of 1
APPLICATION NO. : 11/001866
DATED : September 29, 2009
INVENTOR(S) : T. Wade Fallin and M. Mary Sinnott It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1336 days.

Column 1, Line 15, DELETE "which is identified by".

Signed and Sealed this

Twenty-eighth Day of September, 2010

David J. Kappos
*Director of the United States Patent and Trademark Office*